(12) United States Patent
Miyake et al.

(10) Patent No.: US 7,322,934 B2
(45) Date of Patent: Jan. 29, 2008

(54) ENDOSCOPE

(75) Inventors: Kiyoshi Miyake, Asaka (JP); Mitsuo Obata, Hachioji (JP); Atsushi Miyazaki, Hachioji (JP)

(73) Assignee: Olympus Corporation (JP)

( * ) Notice: Subject to any disclaimer, the term of this patent is extended or adjusted under 35 U.S.C. 154(b) by 456 days.

(21) Appl. No.: 10/877,080

(22) Filed: Jun. 24, 2004

(65) Prior Publication Data

US 2004/0267095 A1  Dec. 30, 2004

(30) Foreign Application Priority Data

Jun. 24, 2003 (JP) .............................. 2003-180095

(51) Int. Cl.
*A61B 1/05* (2006.01)
*A61B 1/07* (2006.01)
*A61B 1/01* (2006.01)

(52) U.S. Cl. ..................... 600/173; 600/114; 600/129; 600/182

(58) Field of Classification Search ................ 600/173, 600/129, 128, 114, 109, 182, 160, 172
See application file for complete search history.

(56) References Cited

U.S. PATENT DOCUMENTS

| 5,166,787 A | * | 11/1992 | Irion | 348/75 |
| 5,305,121 A | * | 4/1994 | Moll | 348/45 |
| 5,653,677 A | * | 8/1997 | Okada et al. | 600/112 |
| 5,782,752 A | * | 7/1998 | Lichtman et al. | 600/137 |
| 5,895,350 A | * | 4/1999 | Hori | 600/167 |
| 5,961,445 A | * | 10/1999 | Chikama | 600/112 |
| 6,986,738 B2 | * | 1/2006 | Glukhovsky et al. | 600/109 |
| 7,001,329 B2 | * | 2/2006 | Kobayashi et al. | 600/114 |
| 2002/0049367 A1 | * | 4/2002 | Irion et al. | 600/173 |
| 2002/0099267 A1 | * | 7/2002 | Wendlandt et al. | 600/173 |
| 2003/0013938 A1 | * | 1/2003 | Iddan et al. | 600/129 |

FOREIGN PATENT DOCUMENTS

| JP | 07-275195 | 10/1995 |
| JP | 07-275196 | 10/1995 |
| JP | 07-275197 | 10/1995 |

* cited by examiner

*Primary Examiner*—John P. Leubecker
(74) *Attorney, Agent, or Firm*—Ostrolenk, Faber, Gerb & Soffen, LLP

(57) ABSTRACT

An endoscope comprises an inserting unit main body, and a head unit that is freely detachably attached to the distal end of the inserting unit main body and that includes an image pickup device which picks up an image of an object and a light emitting element which irradiates illumination light to the object. A holding member holds the head unit such that distal extension of the holding member angles the head unit in a radial direction orthogonal to a longitudinal axis of the distal end of the inserting unit main body.

17 Claims, 20 Drawing Sheets

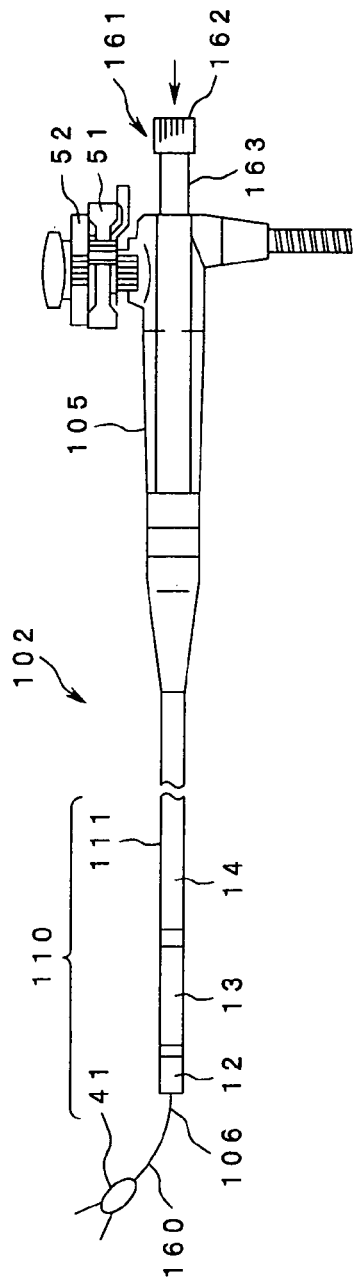
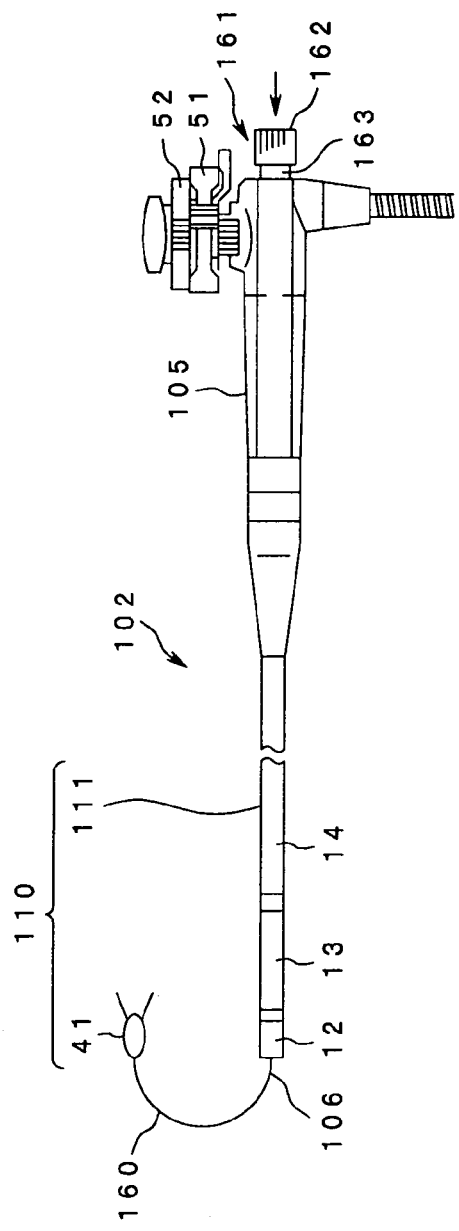

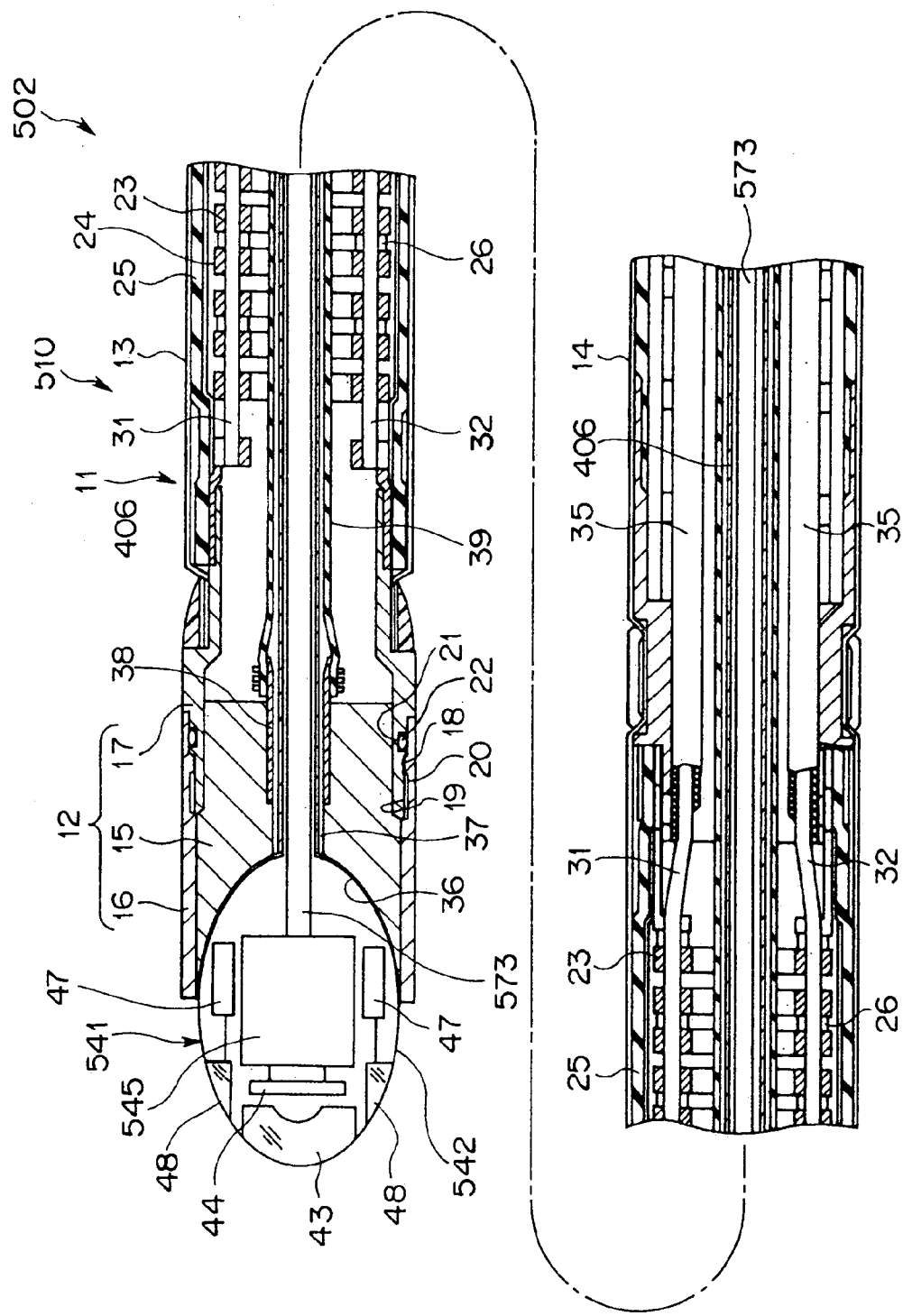

ENDOSCOPE

This application claims the benefit of Japanese Application No. 2003-180095 filed on Jun. 24, 2003, the contents of which are incorporated by this reference.

BACKGROUND OF THE INVENTION

1. Field of the Invention

The present invention relates to an endoscope in which a head unit including a visualizing means is freely detachably attached to the distal end of an inserting unit main body thereof.

2. Description of the Related Art

Endoscope systems have been widely used in the past, wherein an elongated inserting unit of an endoscope is inserted into a body cavity in order to observe an intracavitary organ or to, if necessary, perform various therapeutic procedures using a treatment instrument passed through a treatment channel.

In recent years, a technology for electronic endoscopes has been proposed in, for example, Japanese Patent No. 2966723. According to the technology, an electronic endoscope includes an image pickup unit that is detachable from an endoscope main body. When the endoscope reaches an intended lesion, the image pickup unit incorporated in the distal portion of the endoscope is detached for visualization of the lesion.

According to other conventional electronic endoscope technology, pressure deriving from a jet of fluid is used to cancel magnetic force with which the image pickup unit is fixed to the distal portion of the endoscope so that the image pickup unit can reach an appropriate position in the lesion. Otherwise, a self-propelled means or a self-position collecting means such as a flagellum driver or a caterpillar driver is adapted to the image pickup unit.

Moreover, the image pickup unit is restored to the distal portion of the endoscope using magnetic force generated by an electromagnet or using the self-propelled means or self-position correcting means.

Moreover, as other conventional electronic endoscope technology, a technology according to which a visualizing means is, in addition to an image pickup unit detachable from an endoscope main body, incorporated in the endoscope main body has been proposed in, for example, Japanese Patent No. 2969042.

Furthermore, as other conventional electronic endoscope technology, a mechanism that includes a wire linking an image pickup unit and an endoscope main body and that restores the image pickup unit to a distal portion of the endoscope when the wire is pulled has been proposed in, for example, Japanese Patent No. 2969043.

SUMMARY OF THE INVENTION

An endoscope in accordance with the present invention comprises an inserting unit main body, and a head unit that is freely detachably attached to the distal end of the inserting unit main body and that includes a visualizing means for visualizing an object and an illuminating means for irradiating illumination light to the object.

BRIEF DESCRIPTION OF THE DRAWINGS

FIG. 11 is the first explanatory diagram concerning the movements of a head unit included in the endoscope in accordance with the second embodiment of the present invention;

FIG. 12 is the second explanatory diagram concerning the movements of the head unit included in the endoscope in accordance with the second embodiment of the present invention;

FIG. 24 is a sectional view of an inserting unit of an endoscope in accordance with the fifth embodiment of the present invention.

DETAILED DESCRIPTION OF THE PREFERRED EMBODIMENTS

Figure 1:
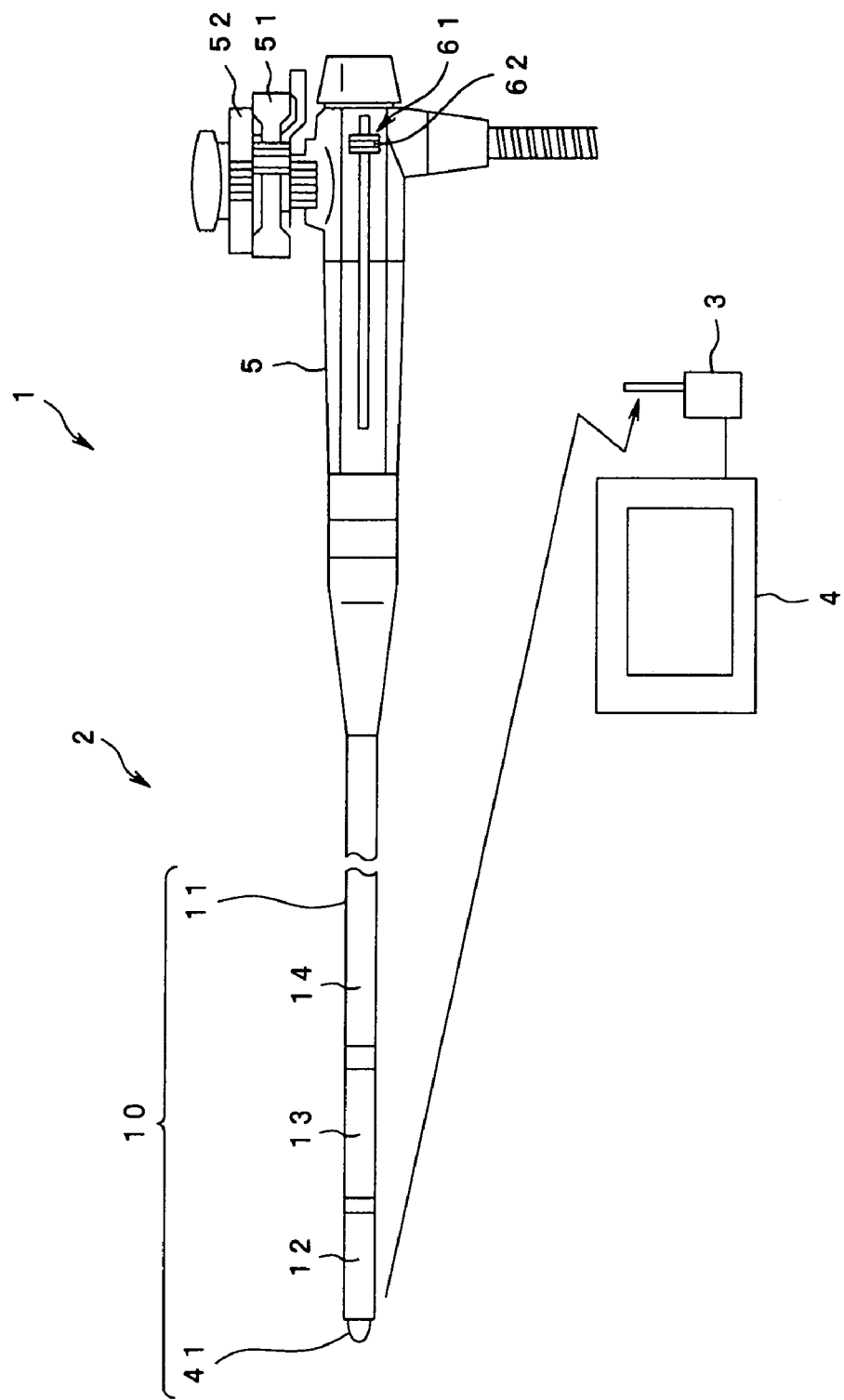
FIG. 1 shows the structure of an electronic endoscope system including a first embodiment of the present invention.

Referring to the drawings, embodiments of the present invention will be described below.

First Embodiment

Figure 2:
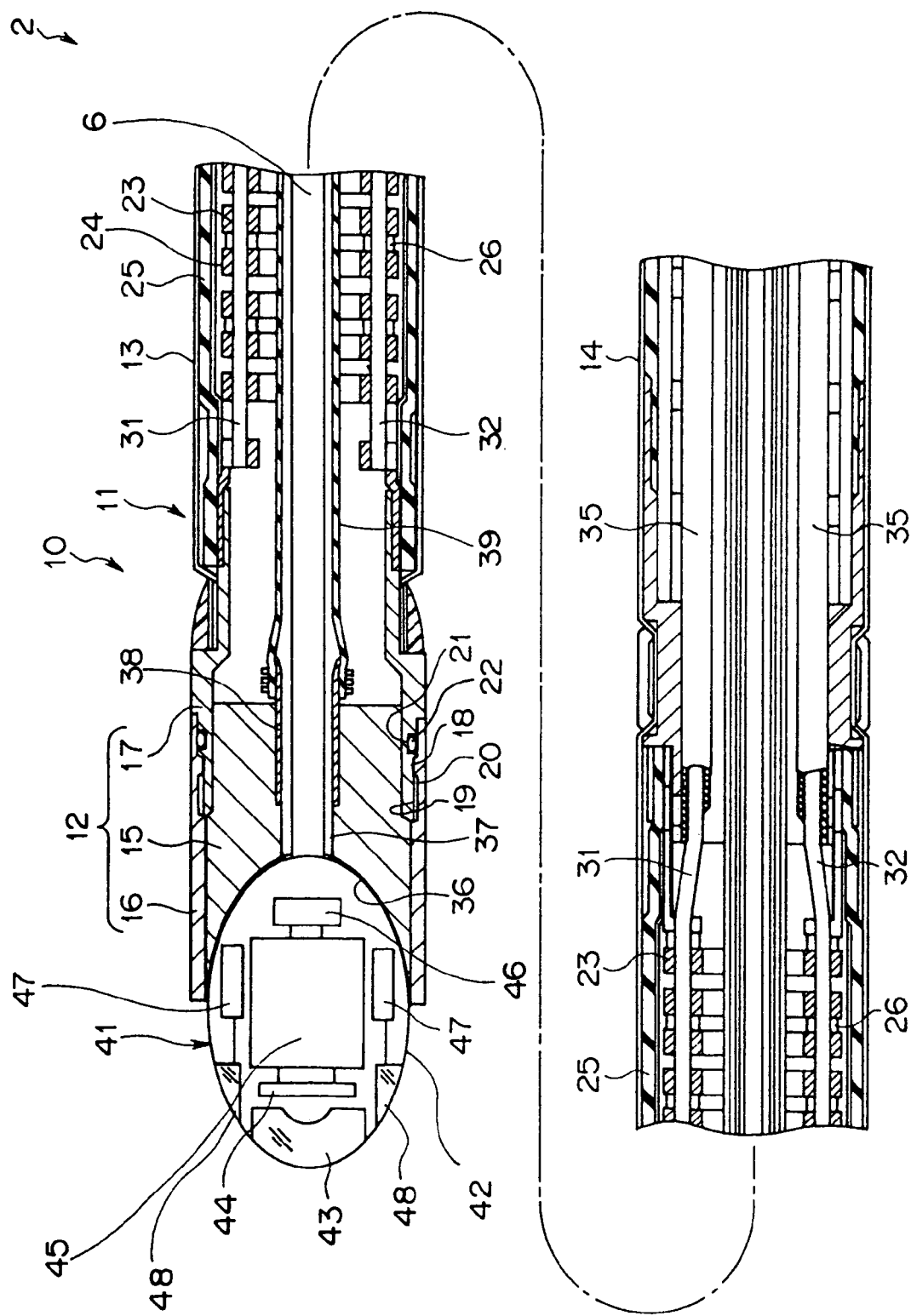
FIG. 2 is a sectional view of an inserting unit of an endoscope in accordance with the first embodiment of the present invention.
Figure 3:
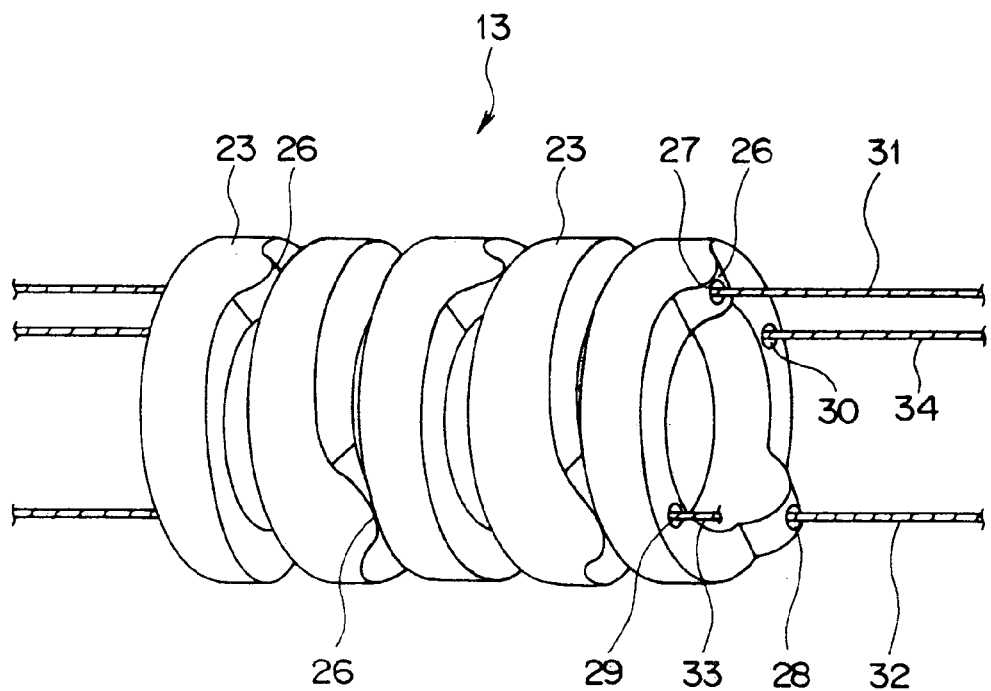
FIG. 3 is a perspective view showing bending pieces incorporated in the inserting unit of the endoscope in accordance with the first embodiment of the present invention.
Figure 4:
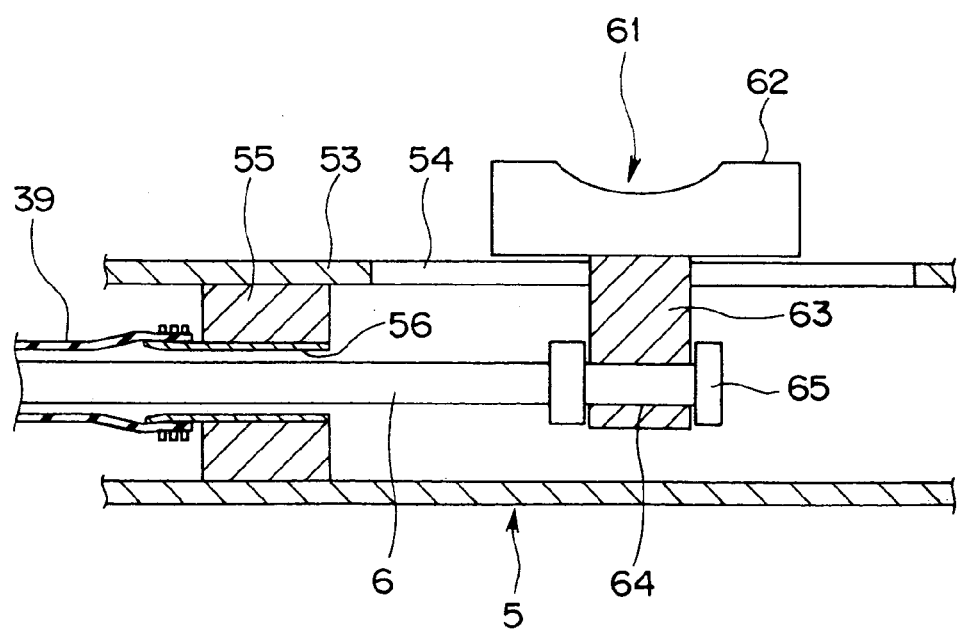
FIG. 4 is a sectional view of an operating unit included in the first embodiment of the present invention.
Figure 5:
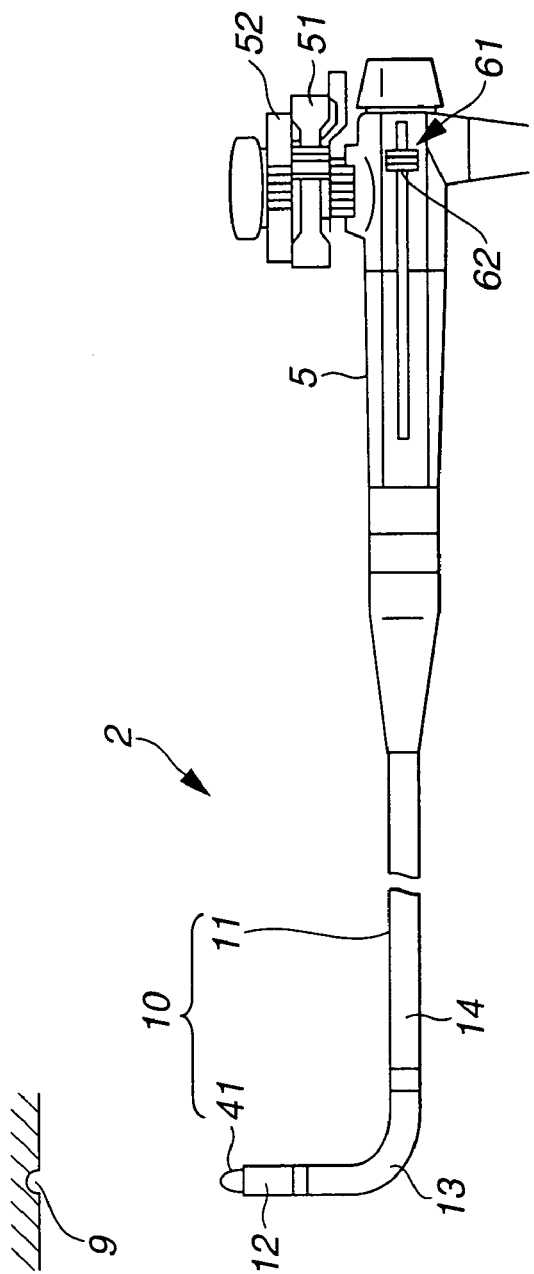
FIG. 5 is the first explanatory diagram concerning the back and forth movements of a head unit included in the endoscope in accordance with the first embodiment of the present invention.
Figure 6:
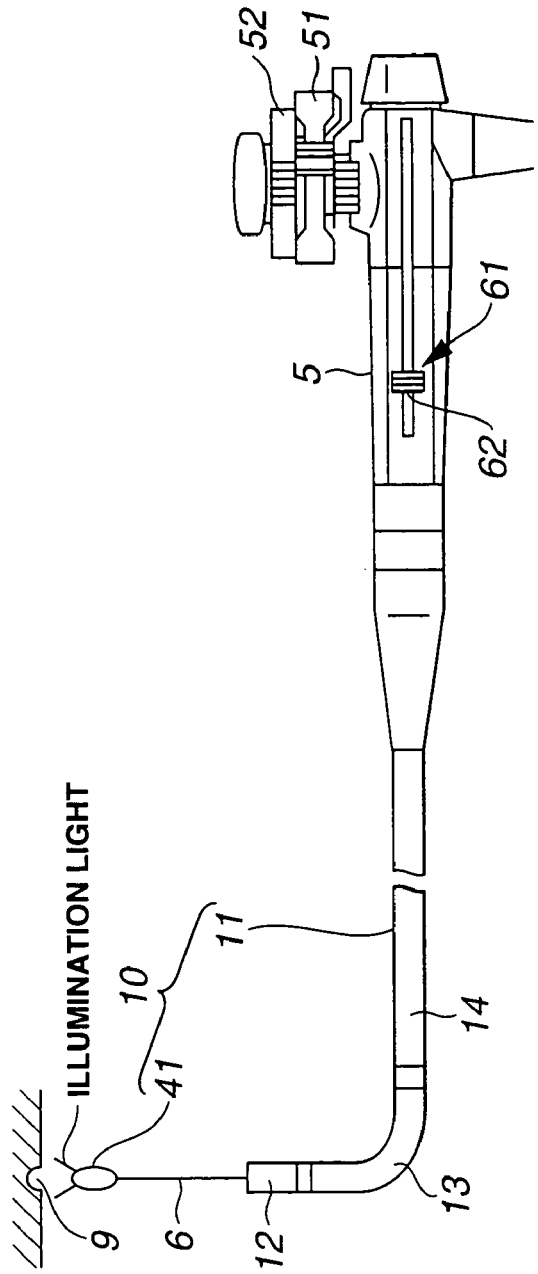
FIG. 6 is the second explanatory diagram concerning the movements of the head unit included in the endoscope in accordance with the first embodiment of the present invention.

FIG. 1 to FIG. 6 are concerned with a first embodiment of the present invention. FIG. 1 shows the structure of an electronic endoscope system. FIG. 2 is a sectional view of an inserting unit of an endoscope. FIG. 3 is a perspective view showing bending pieces incorporated in the inserting unit of the endoscope. FIG. 4 is a sectional view of an operating unit. FIG. 5 is the first explanatory diagram concerning the back and forth movements of a head unit included in the endoscope. FIG. 6 is the second explanatory diagram concerning the movements of the head unit included in the endoscope.

(Structure)

As shown in FIG. 1, an electronic endoscope system 1 comprises an endoscope 2, a receiving unit 3, and a monitor 4.

The endoscope 2 has a large-diameter operating unit 5 coupled to the proximal end of an elongated inserting unit 10.

The inserting unit 10 is inserted into a lumen or the like and includes an inserting unit main body 11 and a capsular head unit 41.

The capsular head unit 41 is freely detachably attached to the distal end of the inserting unit main body 11.

The inserting unit main body 11 has a rigid distal-portion main body 12, a bending section 13, and a flexible tube 14 concatenated in that order from the distal end thereof. A holding member 6 shown in FIG. 2 lies through the inserting unit main body 11. As shown in FIG. 1, the proximal end of the inserting unit main body 11 is coupled to the operating unit 5.

The bending section 13 is freely bendable, whereby the distal-portion main body 12 can be displaced and angled in a desired direction. The flexible tube 14 is elongated, soft, and flexible.

As shown in FIG. 2, the distal-portion main body 12 includes a distal-portion component part 15, a distal outer frame 16, and a proximal outer frame 17.

The distal-portion component part 15 is an internal structure of the distal-portion main body 12 and made of a metal.

The distal external surface of the distal-portion component part 15 and the distal internal surface of the outer frame 16 are bonded with an adhesive in a fluid-tight manner.

A gap 18 is created between the proximal external surface of the distal-portion component part 15 and the proximal internal surface of the outer frame 16.

A female screw 19 is threaded on the proximal internal surface of the outer frame 16. A male screw 20 and a circumferential groove 21 are formed on the distal external surface of the outer frame 17 in that order from the distal end of the outer frame 17.

The distal part of the outer frame 17 is inserted into the gap 18. When the female screw 19 and male screw 20 are meshed with each other, the distal part of the outer frame 17 is fitted in the gap 18.

An O ring 22 is put in the groove 21, whereby the outer frames 16 and 17 are engaged with each other in a fluid-tight manner.

The bending section 13 is formed at the rear end of the outer frame 17 of the distal-portion main body 12. A bending tube 24 having a plurality of bending pieces 23 concatenated in series with one another is incorporated in the bending section 13. The external surface of the bending tube 24 is covered with a bending rubber 25 made of fluoro-rubber or the like.

The bending pieces 23 are incorporated in the bending section 13 so that each of the bending pieces 23 can, as shown in FIG. 3, pivot on a fulcrum 26.

As shown in FIG. 2 and FIG. 3, four angling wires 31, 32, 33, and 34 are terminated at upward, downward, rightward, and leftward positions near the distal end of the bending section 13. The angling wires are used to apply tensile force to the distal part of the bending section 13 so that the plurality of bending pieces 23 will pivot in the direction to which the tensile force is applied.

Each of the bending pieces 23 has through holes 27, 28, 29, and 30 formed at positions therein corresponding to the upward, downward, rightward, and leftward positions in the distal part of the bending section 13. The angling wires 31, 32, 33, and 34 are passed through the through holes 27, 28, 29, and 30 respectively.

Four coil pipes 35 for holding the angling wires 31, 32, 33, and 34 respectively are incorporated in the flexible tube 14.

The proximal ends of the angling wires 31, 32, 33, and 34 are coupled to angling knobs 51 and 52 for upward or downward angling or for rightward or leftward angling included in the operating unit 5 shown in FIG. 1.

When the angling knobs 51 and 52 for upward or downward angling or for rightward or leftward angling shown in FIG. 1 are manipulated, the angling wires 31, 32, 33, and 34 shown in FIG. 3 are pulled.

Next, the capsular head unit 41 will be described below.

As shown in FIG. 2, the capsular head unit 41 is freely detachably attached to the distal-portion main body 12. A capsular case 42 of the capsular head unit 41 accommodates an objective optical system 43, a CCD type solid-state image pickup device 44, a camera control unit 45, a transmitting unit 46, a power supply unit 47, and light emitting diodes (hereinafter LEDS) 48 that are light emitting elements serving as an illuminating means. The objective optical system 43 and CCD type solid-state image pickup device 44 constitute a visualizing means.

The power supply unit 47 supplies power to each of the camera control unit 45, transmitting unit 46, and LEDS 48.

The distal-portion component part 15 included in the distal-portion main body 12 has a recess 36 in which the proximal part of the capsular head unit 41 is fitted. The distal-portion component part 15 has a through hole 37 bored axially. A base 38 is attached to the proximal part of the through hole 37 bored in the distal-portion component part 15.

The objective optical system 43 and LEDs 48 are located near the distal end (front) of the case 42 of the capsular head unit 41. The CCD type solid-state image pickup device 44 is located at the position where images are formed optical system 43. The camera control unit 45 is located behind the CCD type solid-state image pickup device 44. The transmitting unit 46 is attached to the proximal end of the camera control unit 45. The transmitting unit 46 is a transmitting means for transmitting an image signal that represents an object of which image is picked up by the CCD type solid-state image pickup device 44.

Moreover, the holding member 6 that serves as a holding means for holding the capsular head unit 41, which will be described later, so that the capsular head unit 41 can be freely separated from or restored to the distal-portion component part 15 is coupled to the rear end of the case 42 of the capsular head unit 41.

Next, the holding member 6 will be described below.

The holding member 6 has a predetermined length and is formed with a single wire that is made of a super-elastic alloy and that elastically deforms with extraneous force whose strength is of a certain level or higher.

Furthermore, the holding member 6 that is an elastic member is sheathed in and supported by a protective tube 39 whose one end is coupled to the distal-portion main body 12. The protective tube 39 is fixed to the base 38 attached to the distal-portion component part 15 of the distal-portion main body 12 by means of bonding, winding of a thread, or press fitting.

Next, a holding member manipulation lever 61 for use in manipulating the holding member 6 will be described in conjunction with FIG. 4.

As shown in FIG. 4, the holding member manipulation lever 61 that is a manipulating means has an operating unit 62 and a lever base 63 integrated thereinto. A penetrating hole 64 is bored in the lever base 63.

On the other hand, a slit 54 is formed in a case 53 of the operating unit 5. The lever base 63 is inserted into the slit 54 so that the lever base 63 can slide in the longitudinal direction of the operating unit 5.

Inside the case 53, the proximal end of the holding member 6 is engaged in the penetrating hole 64 of the lever base 63 using an engaging base 65.

An annular member 55 is put on the internal surface of the case 53 ahead of the slit 54, that is, in the proximal part of the case 53. A base 56 is fitted into the bore of the annular member 55.

The protective tube 39 is fixed to the base 56 within the operating unit 5. Herein, the protective tube 39 is fixed to the base 56 in the same manner as it is fixed to the base 38.

Owing to the foregoing structure, the capsular head unit 41 is freely detachably attached to the distal end of the inserting unit main body 11.

The objective optical system 43, CCD type solid-state image pickup device 44, and camera control unit 45 are incorporated in the capsular head unit 41, and constitute the visualizing means for visualizing an object.

The LEDs 48 are incorporated in the capsular head unit 41 and serve as the illuminating means for irradiating illumination light to the object.

The holding member 6 serves as moving means for moving the capsular head unit 41 back and forth so that the capsular head unit 41 will be attached or detached to or from the distal end of the inserting unit main body 11. At this time, the holding member manipulation lever 61 is manipulated so that while the capsular head unit 41 is held by the holding member 6, the capsular head unit 41 will be separated from or restored to the distal end of the inserting unit main body 11 in an axial direction of the inserting unit main body 11.

(Operation)

Next, the operation of the first embodiment will be described below.

When the endoscope 2 is used for examination, the inserting unit main body 11 is inserted into a lumen or the like that is an object to be examined.

At this time, the capsular head unit 41 is kept attached to the distal end of the distal-portion main body 12.

When the inserting unit reaches a desired position to be examined in the object, the operator manipulates the angling knobs 51 and 52 so as to bend the bending section 13, and thus angles the objective optical system 43 included in the capsular head unit 41 in the direction of a region 9 the operator want to observe.

Thereafter, as shown in FIG. 6, the holding member manipulation lever 61 is moved toward the distal end of the operating unit. Consequently, the lever base 63 shown in FIG. 4 pushes the locking base 65. This causes the holding member 6 to move, as shown in FIG. 6, forward, that is, to the distal end of the endoscope. At this time, since the holding member 6 is made of a super-elastic alloy as mentioned previously, although the holding member 6 lies through the bending section 13, the holding member 6 can deform in line with the bent shape of the bending section 13 responsively to extraneous force applied for bending. The holding member 6 is then jutted out of the distal-portion main body 12, and causes the capsular head unit 41 to advance to the desired position. Thereafter, the holding member manipulation lever 61 is halted. Incidentally, the wire material of the super-elastic alloy elastically deforms responsively to extraneous force whose strength is of a certain level or higher. If the extraneous force is weak, when the small capsular head unit 41, for example, is kept attached to the distal end of the inserting unit main body, the elasticity of the super-elastic alloy surpasses the weight of the capsular head unit 41. The capsular head unit 41 is therefore linearly jutted out of the distal-portion main body 12. Consequently, by manipulating the holding member manipulation lever 61, the capsular head unit 41 can be freely separated from or restored to the axial direction of the inserting unit main body 11.

When the capsular head unit 41 is used for visualization, illumination light is irradiated from the LEDs 48 shown in FIG. 2 to the region 9. Light reflected from the region 9 is concentrated on the imaging area of the CCD type solid-state image pickup device 44 via the objective optical system 43, and an image is picked up by the CCD type solid-state image pickup device 44. An image pickup signal sent from the CCD type solid-state image pickup device 44 is converted into image data by the camera control unit 45.

The transmitting unit 46 transmits necessary image data sent from the camera control unit 45, and the receiving unit 3 disposed outside the object receives the image data. Eventually, an image is displayed on the monitor 4 connected to the receiving unit 3.

(Advantages)

According to the endoscope of the first embodiment, the capsular head unit 41 including the visualizing means is freely detachably attached to the distal end of the inserting unit main body 11. A range of illumination can be shifted with the movement of the capsular head unit 41. Consequently, illumination light can be irradiated in such a manner that an optimal view image will be formed. Therefore, an appropriate illuminance can be ensured all the time and a stable visualization capability can be maintained.

Talking of a conventional endoscope, after the endoscope is angled, it is structurally hard to advance the endoscope in the direction of the field of view. In contrast, as far as the endoscope in accordance with the first embodiment of the present invention is concerned, the capsular head unit 41 can be readily located at a desired position. Examination can therefore be achieved efficiently.

Moreover, conventionally, when an endoscope is located closely to a region to be observed, optical zooming or electronic zooming must be employed. However, the optical zooming has a drawback that an optical system becomes large in size, and the electronic zooming has a drawback that the resultant image is so coarse that it is unsuitable for close examination. According to the first embodiment, the drawbacks are overcome.

Furthermore, according to the first embodiment, the capsular head unit 41 accommodates all facilities relevant to visualization or illumination. Therefore, the conventionally employed image pickup cable and illumination light guide fiber need not be passed through the inserting unit main body 11. The inserting unit main body 10 can therefore be designed thinly.

Second Embodiment

Figure 7:
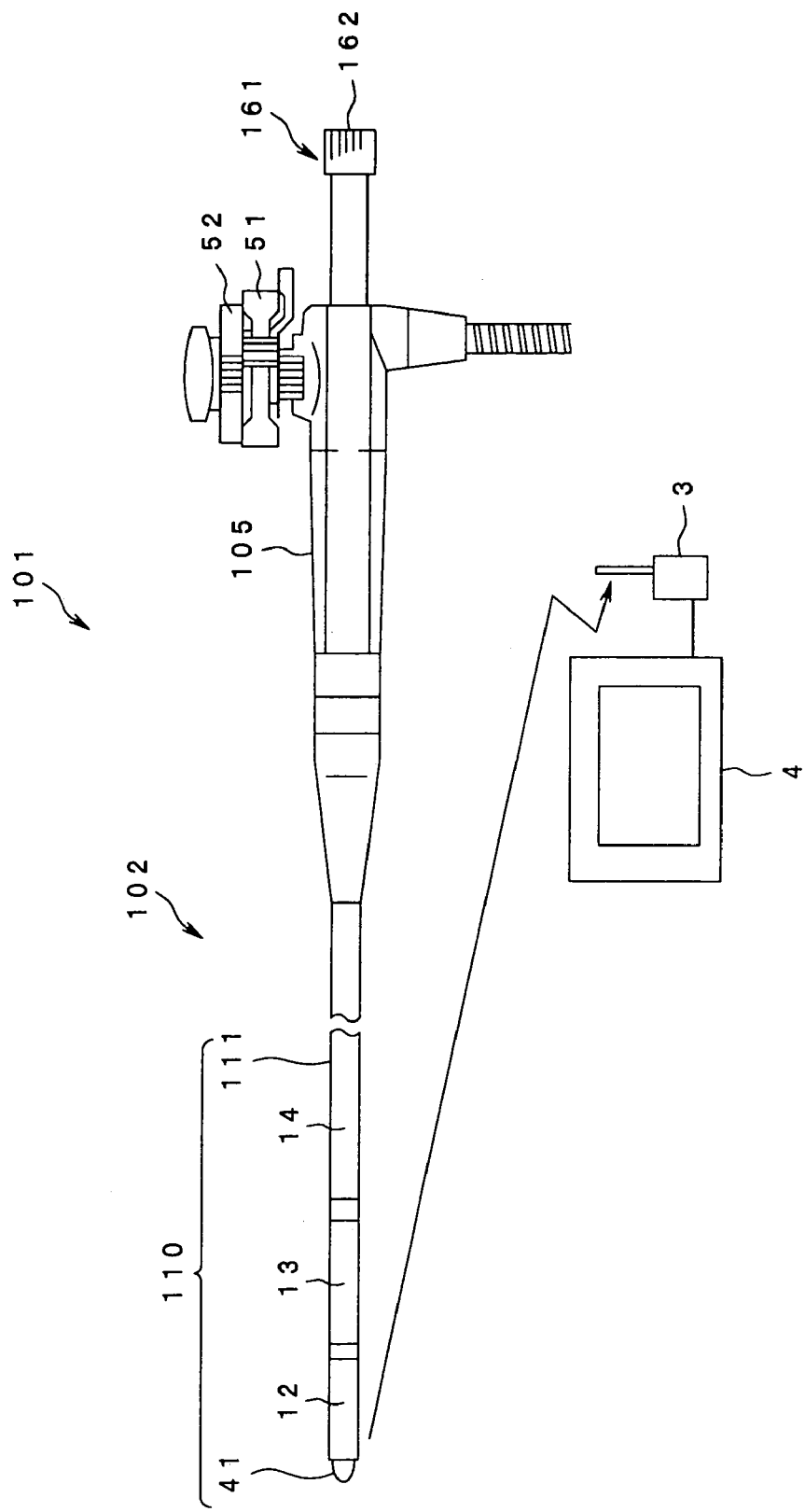
FIG. 7 shows the structure of an electronic endoscope system including a second embodiment of the present invention.
Figure 8:
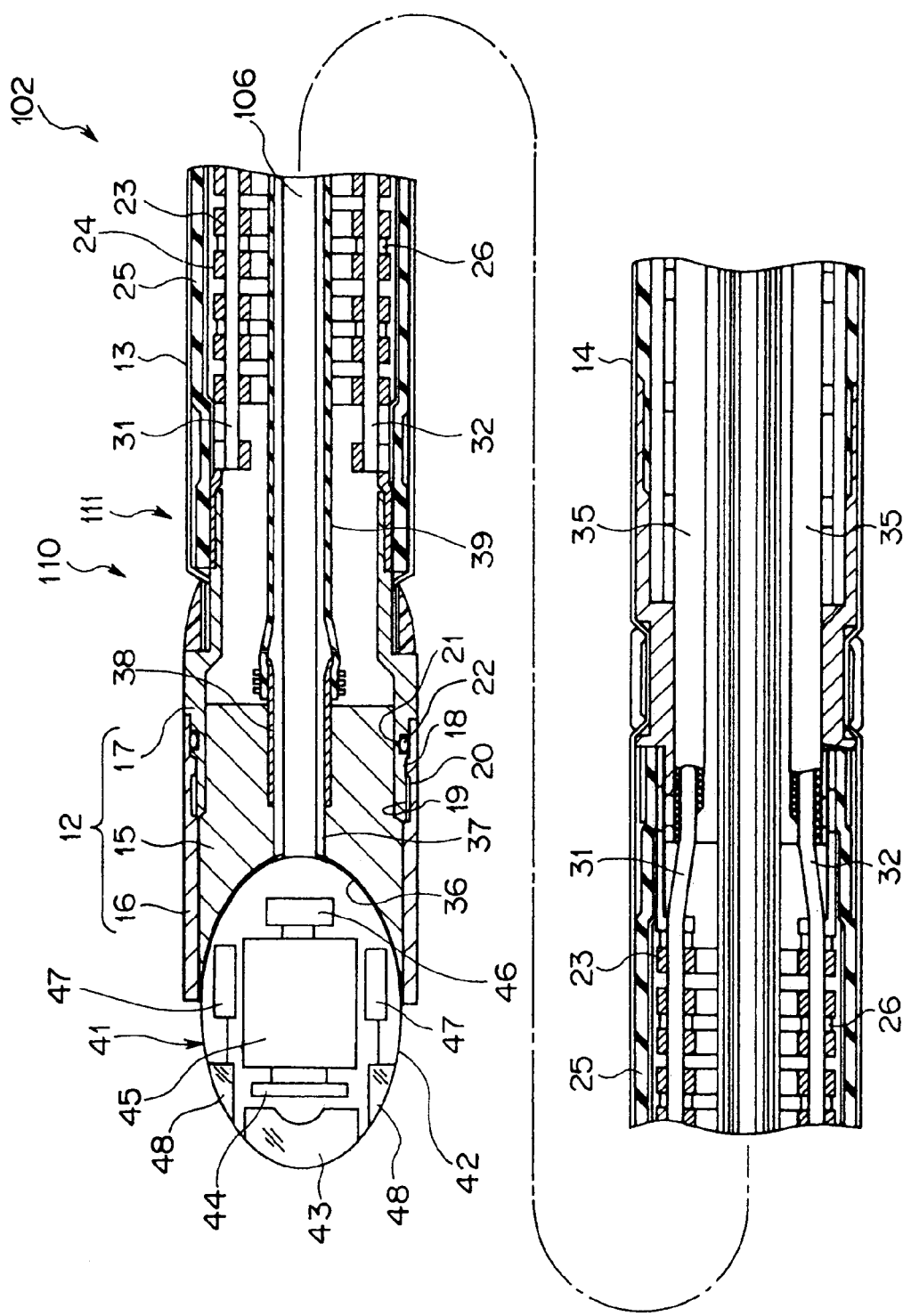
FIG. 8 is a sectional view of an inserting unit of an endoscope in accordance with the second embodiment of the present invention.
Figure 9:
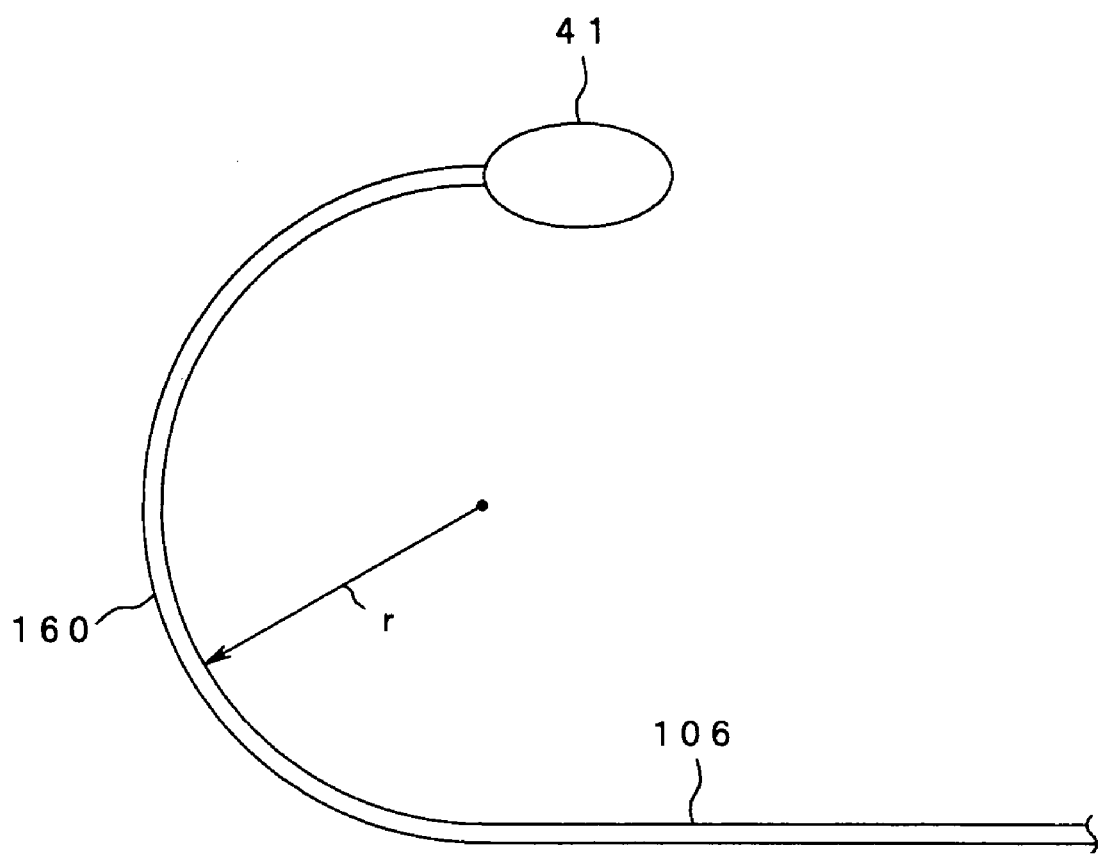
FIG. 9 is a side view showing a guide member included in the endoscope in accordance with the second embodiment of the present invention.
Figure 10:
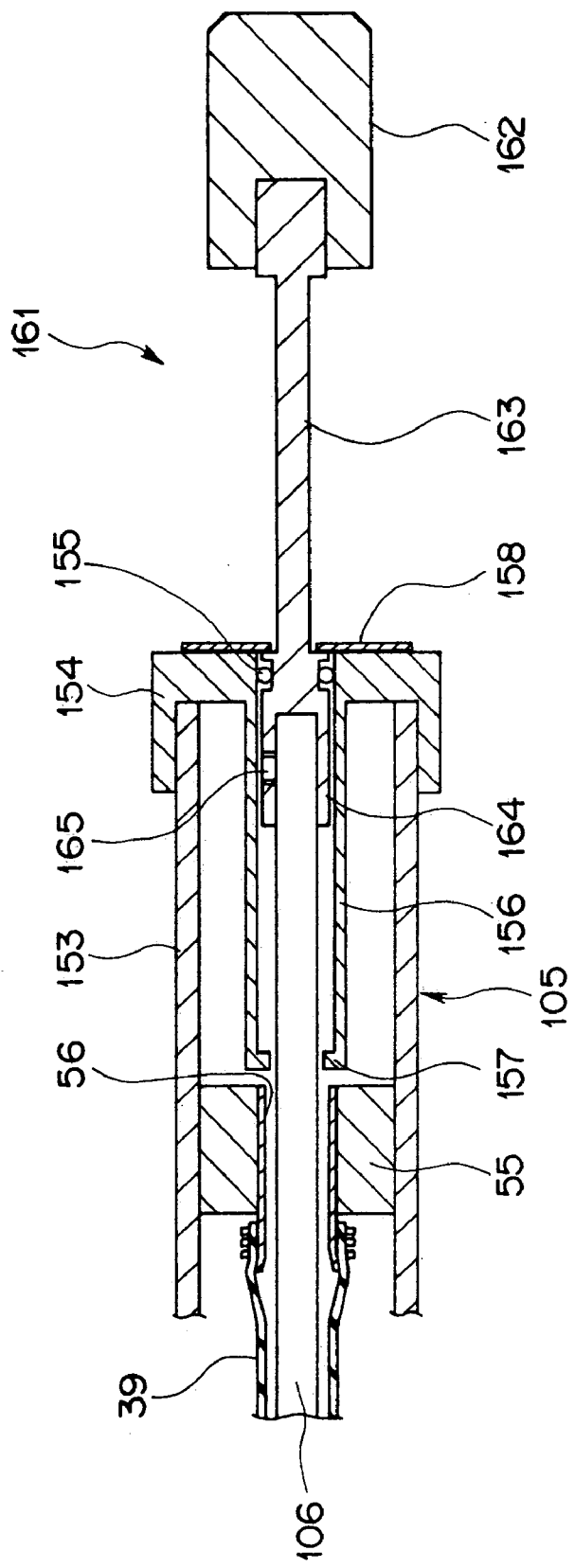
FIG. 10 is a sectional view of an operating unit included in the second embodiment of the present invention.
Figure 13:
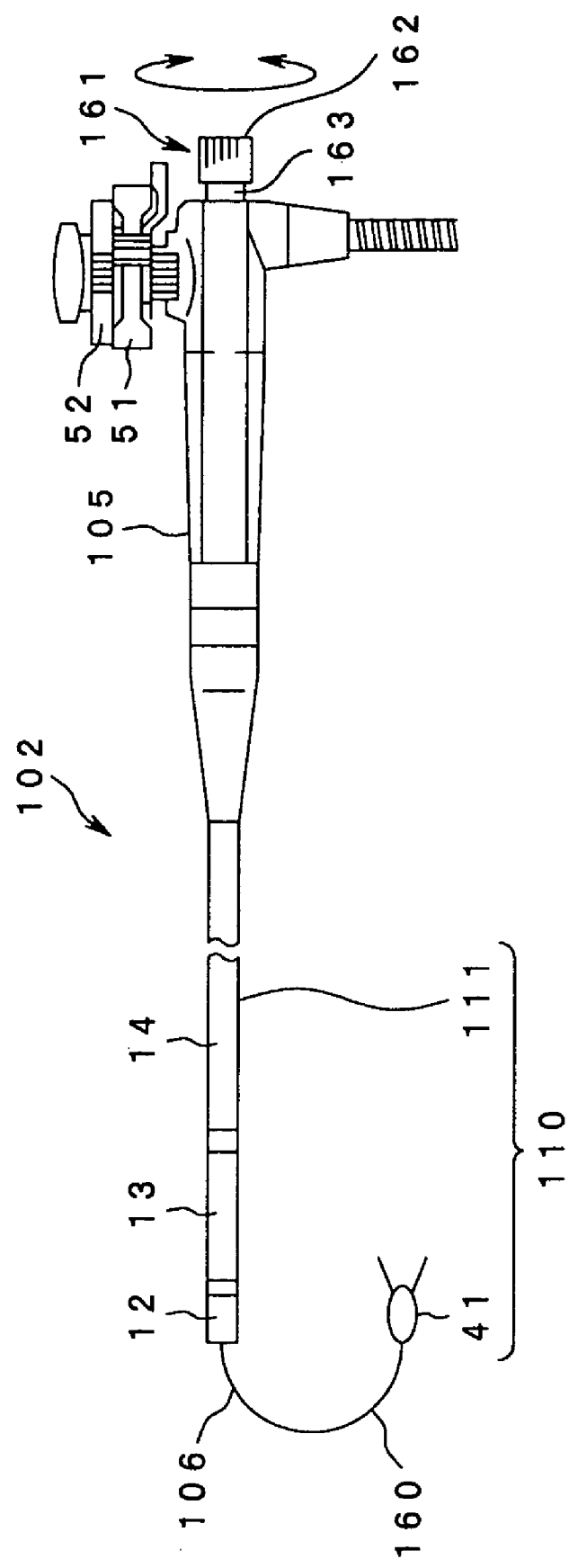
FIG. 13 is the third explanatory diagram concerning the movements of the head unit included in the endoscope in accordance with the second embodiment of the present invention.

FIG. 7 to FIG. 13 are concerned with a second embodiment of the present invention. FIG. 7 shows the structure of an electronic endoscope system. FIG. 8 is a sectional view of an inserting unit of an endoscope. FIG. 9 is a side view showing a guide member incorporated in the endoscope. FIG. 10 is a sectional view of an operating unit. FIG. 11 is a first explanatory diagram concerning the movements of a head unit included in the endoscope. FIG. 12 is a second explanatory diagram concerning the movements of the head unit included in the endoscope. FIG. 13 is a third explanatory diagram concerning the movements of the head unit included in the endoscope.

For the description of the second embodiment to be made in conjunction with FIG. 7 to FIG. 13, the same reference numerals will be assigned to components identical to those of the first embodiment shown in FIG. 1 to FIG. 6. The description of the components will be omitted.

(Structure)

As shown in FIG. 7, an electronic endoscope system 101 comprises an endoscope 102, a receiving unit 3, and a monitor 4.

The endoscope 102 has a large-diameter operating unit 105 coupled to the proximal end of an elongated inserting unit 110.

The inserting unit 110 is inserted into a lumen and includes an inserting unit main body 111 and a capsular head unit 41.

The capsular head unit 41 is freely detachably attached to the distal end of the inserting unit main body 111.

The inserting unit main body 111 has a distal-portion main body 12, a bending section 13, and a flexible tube 14 concatenated in that order from the distal end thereof. A guide member 106 shown in FIG. 8 lies through the inserting unit main body 111.

As shown in FIG. 7, the proximal end of the inserting unit main body 111 is coupled to the operating unit 105.

As shown in FIG. 8, instead of the holding member 6 included in the first embodiment (see FIG. 2), the guide member 106 is coupled as a holding means, which holds the capsular head unit 41 so that the capsular head unit 41 can be freely separated from or restored to the inserting unit main body, to the capsular head unit 41. The guide member 106 is, as shown in FIG. 9, made of a super-elastic alloy and includes a bendable portion 160 that is bendable at a radius of curvature r to have a predetermined bent shape.

As shown in FIG. 8, the guide member 106 is entirely sheathed in a protective tube 39 lying through the inserting unit main body 11.

As shown in FIG. 10, the proximal (user-side) end of the guide member 106 is coupled to a guide member manipulation member 161.

The guide member manipulation member 161 serving as manipulating means has a linkage shaft 163 embedded in the distal-end side of a guide member manipulation handle 162. A piston 164 is formed at the distal end of the linkage shaft 163.

On the other hand, a casing 154 is attached to the proximal end of a main body case 153 of the operating unit 105. The casing 154 has a cylinder 156 jutted distally.

The guide member 106 is locked in the piston 164 formed at the distal end of the linkage shaft 163 while being pressed by a screw 165.

Furthermore, the linkage shaft 163 is held in the cylinder 156 of the casing 154 with an O ring 155 therebetween. With the gap between the linkage shaft 163 and the cylinder 156 kept watertight, the linkage shaft 163 can be freely rotated about the axis thereof and can be axially pulled or thrust back and forth.

Incidentally, stoppers 157 and 158 for restricting the magnitude of movement made by the piston 164 are fixed to the distal end and proximal end of the cylinder 156 of the casing 154.

Owing to the structure, when the linkage shaft 163 of the guide member manipulation handle 162 included in the operating unit 105 is axially moved back and forth, the capsular head unit 41 can be freely separated from or restored to the distal end of the distal-portion component part 15 in an axial direction of the inserting unit main body 111 or in a radial direction thereof.

The guide member 106 and guide member manipulation member 161 constitute a first visualizing direction changing means that holds the capsular head unit 41 so that a visualizing direction in which the capsular head unit 41 visualizes an object can be set to any direction and the capsular head unit 41 can be freely separated from or restored to the distal end of the inserting unit main body 111.

The bending section 13 and angling knobs 51 and 52 constitute a second visualizing direction changing means for changing the visualizing direction of the capsular head unit 41 to any direction.

(Operation)

When the endoscope 102 of the second embodiment shown in FIG. 7 is used for examination, the inserting unit main body 111 is inserted into a lumen or the like that is an object to be examined. At this time, the capsular head unit 41 is kept attached to the distal-portion main body 12.

When the inserting unit main body 111 reaches a region that must be examined in detail, the guide member manipulation handle 162 is thrust forward. Consequently, as shown in FIG. 11, the linkage shaft 163 and guide member 106 are thrust forward. This causes the capsular head unit 41 coupled to the distal end of the guide member 106 to jut out of the distal-portion main body 12.

At this time, since the guide member 106 has the bendable portion 160, the capsular head unit 41 is jutted out along a curve defined with the radius of curvature at which the bendable portion 160 of the guide member 106 is bendable. Namely, by manipulating the guide member manipulation handle 162, the capsular head unit 41 can be freely separated from or restored to the inserting unit main body 111 in a radial direction of the inserting unit main body 111, that is, in a direction orthogonal to the axis thereof.

When the guide member manipulation handle 162 is further thrust forward, a large part of the bendable portion 160 is, as shown in FIG. 12, jutted out of the distal-portion main body 12. The bendable portion 160 is jutted out until the capsular head unit 41 is nearly turned over.

Furthermore, if a region to be examined cannot be visualized in the state shown in FIG. 12, the position of the capsular head unit 41 is, as shown in FIG. 13, changed circumferentially with respect to the inserting unit main body 111 by rotating the guide member manipulation handle 162.

Specifically, the capsular head unit 41 can be led to any of upward, downward, rightward, and leftward directions within 360° by thrusting, pulling, or rotating the guide member manipulation handle 162. In other words, the capsular head unit 41 can be not only freely separated from or restored to the inserting unit main body in a radial direction of the inserting unit main body 111 but also rotated about the axis of the inserting unit main body 111.

(Advantages)

The second embodiment provides the same advantages as the first embodiment does. In addition, since the bendable portion 160 is included, the capsular head unit 41 can be not only moved in an axial direction of the inserting unit main body 111 but also led three-dimensionally. This leads to an increase in a range that can be examined. Moreover, an object of examination can be accessed more readily.

Figure 14:
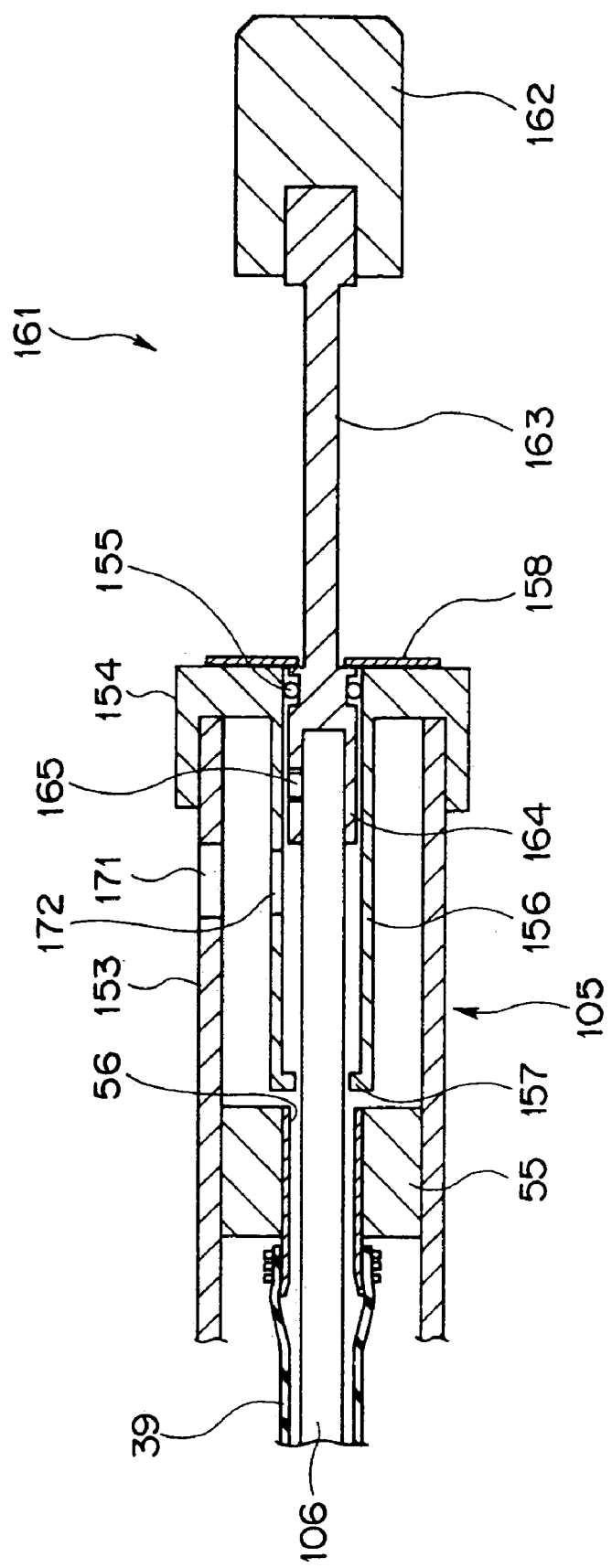
FIG. 14 is an explanatory diagram showing a variant of the second embodiment of the present invention.

FIG. 14 is an explanatory diagram showing a variant of the second embodiment.

A description will be made of the variant in conjunction with FIG. 14 on the assumption that the components other than those illustrated are identical to those of the second embodiment shown in FIG. 7 to FIG. 13.

Incidentally, conventional endoscopes include an endoscope for industrial use that is inserted into, especially, pipes or a gas turbine in order to visualize the interior thereof. The outermost layer of an inserting unit of such an endoscope is rubbed against the walls of pipes, whereby the periphery of the inserting unit of the endoscope may be finely flawed or smeared. In quite a few cases, the inserting unit main body may have to be replaced with a new one because of the flaws or smear.

However, since the conventional endoscope has a solid-state image pickup device or a light guide fiber incorporated therein, it takes much time to disassemble the endoscope.

In the variant shown in FIG. 14, once a screw 165 is removed through a window 171 formed in the main body case 153 of the operating unit 105 and a window 172 formed in the cylinder 156, the guide member 106 can be taken out. Consequently, the assembly of the capsular head unit 41 and guide member 106 shown in FIG. 9 can be readily dismounted. Namely, in the endoscope of the present variant, since the capsular head unit 41 accommodates all visualization facilities, once the guide member 106 is freed by removing the screw 165, the inserting unit main body 111 and operating unit 105 shown in FIG. 7 are separated from each other. The inserting unit main body 111 can be readily replaced with a new one.

In order to mount a new inserting unit main body 111, the guide member 106 is passed through the protective tube 39 from the distal-portion main body 12. The linkage shaft 163 and guide member 106 are then screwed through the windows 171 and 172.

The structure to which the windows and linkage shaft included in the present variant are adapted is not limited to that of the second embodiment. Alternatively, the windows may be formed in the holding member 6 included in the first embodiment.

Furthermore, when the capsular head unit 41 has an explosion-proof structure, if the monitor 4 and others are located in other place, fully explosion-proof examination can be achieved.

Third Embodiment

Figure 15:
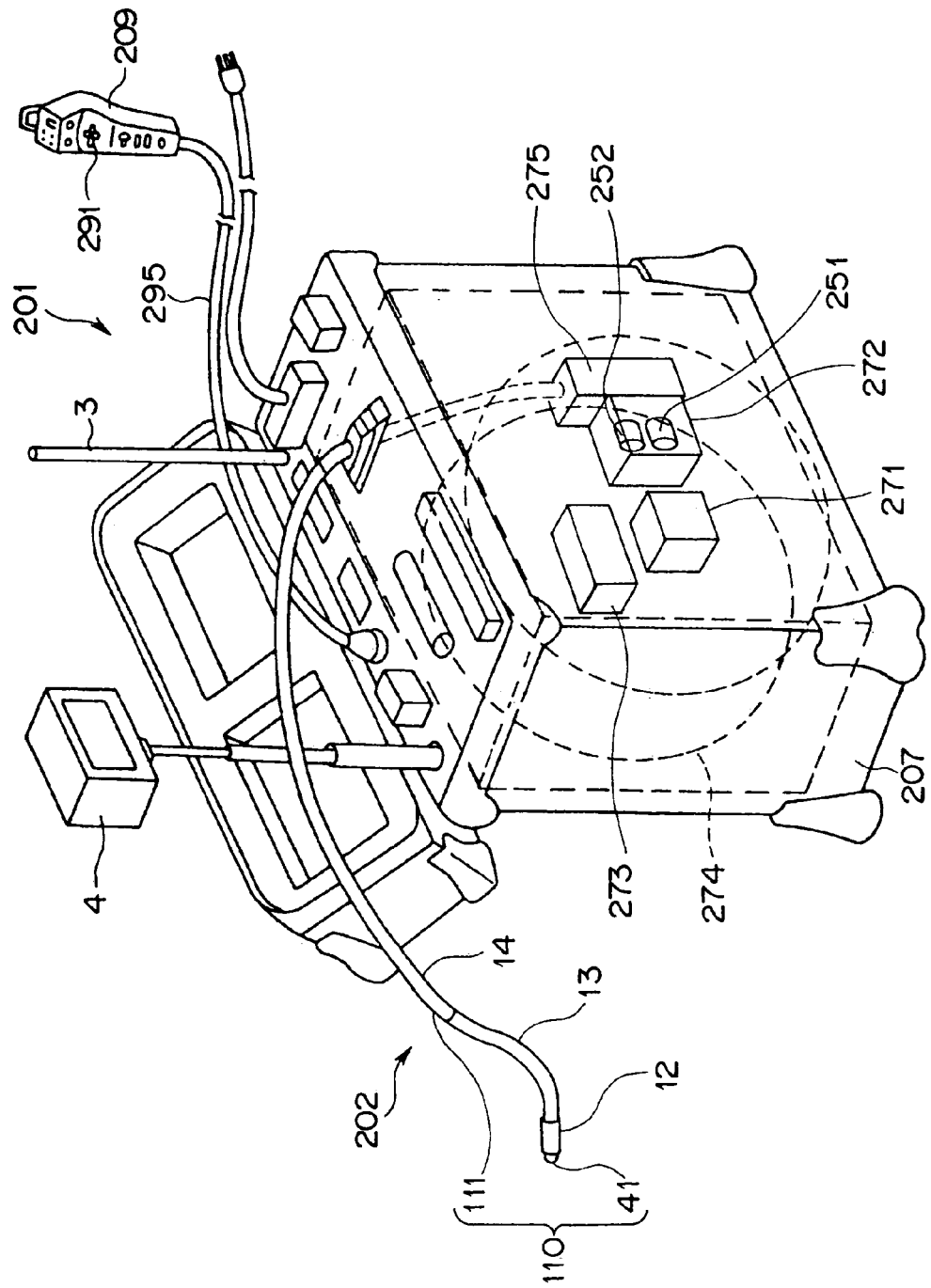
FIG. 15 is a perspective view of an electrically angled endoscope system including a third embodiment of the present invention.
Figure 16:
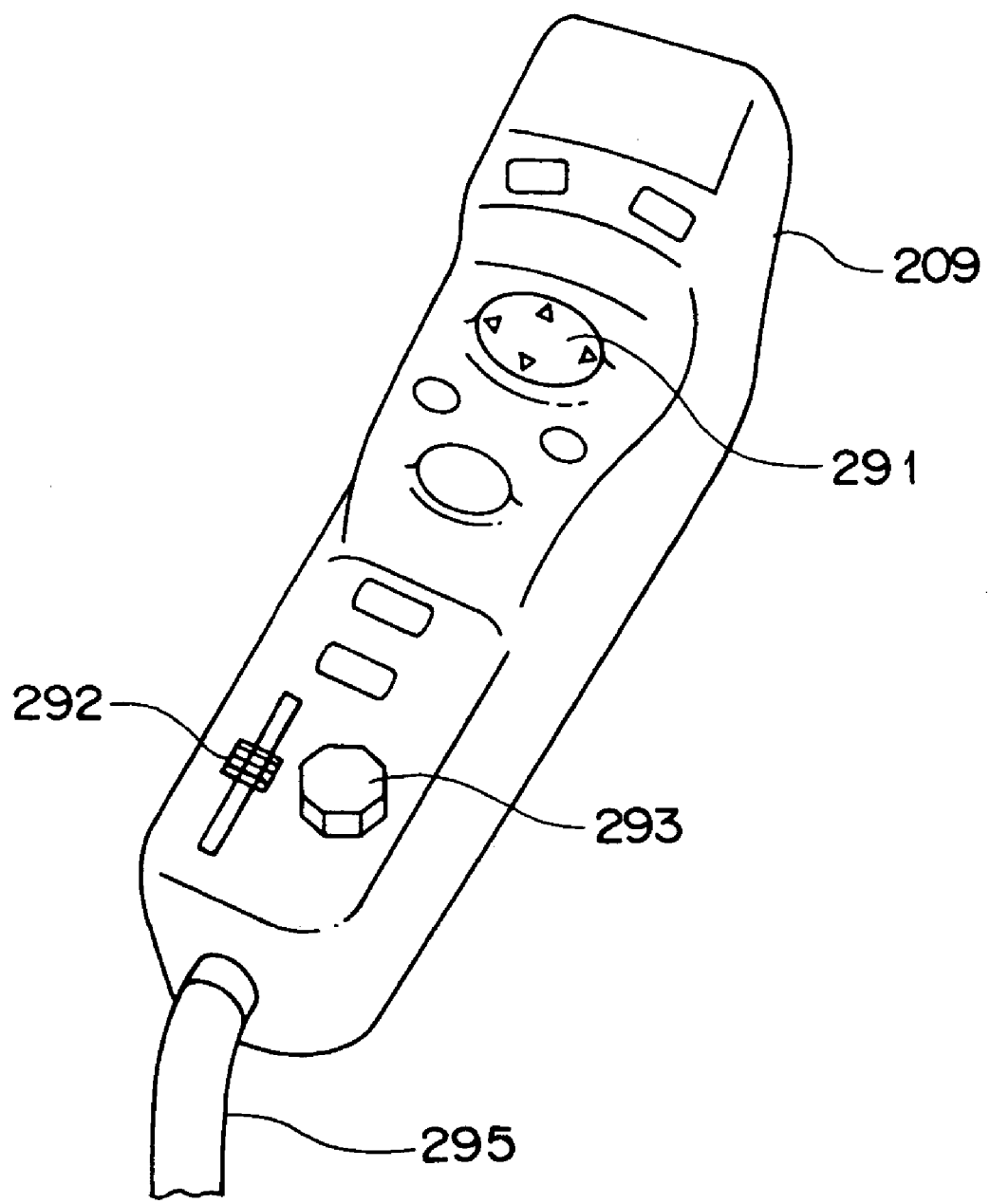
FIG. 16 is a perspective view of a remote controller employed in the endoscope system including the third embodiment of the present invention.
Figure 17:
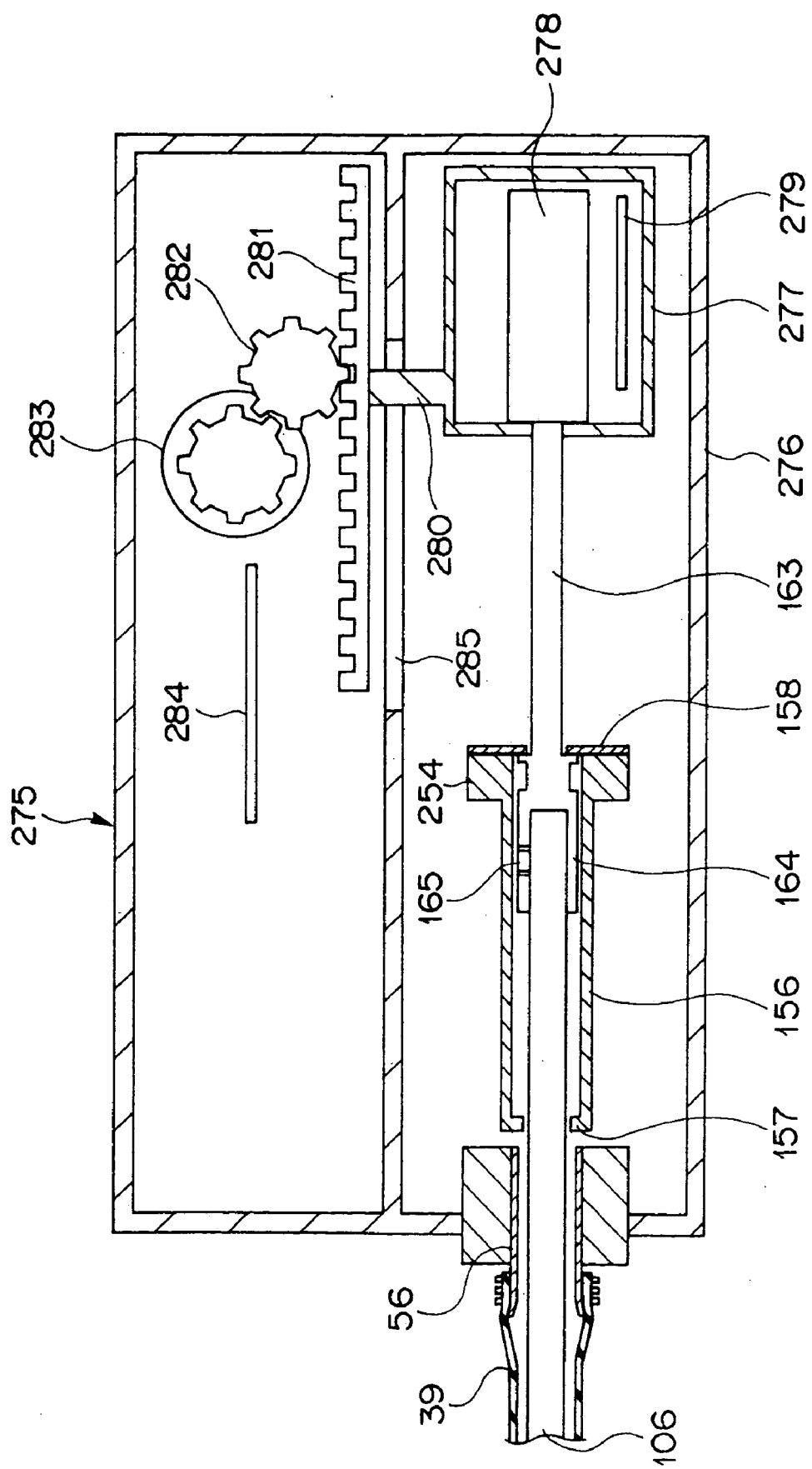
FIG. 17 is a sectional view of a driving motor unit included in the third embodiment of the present invention.
Figure 18:
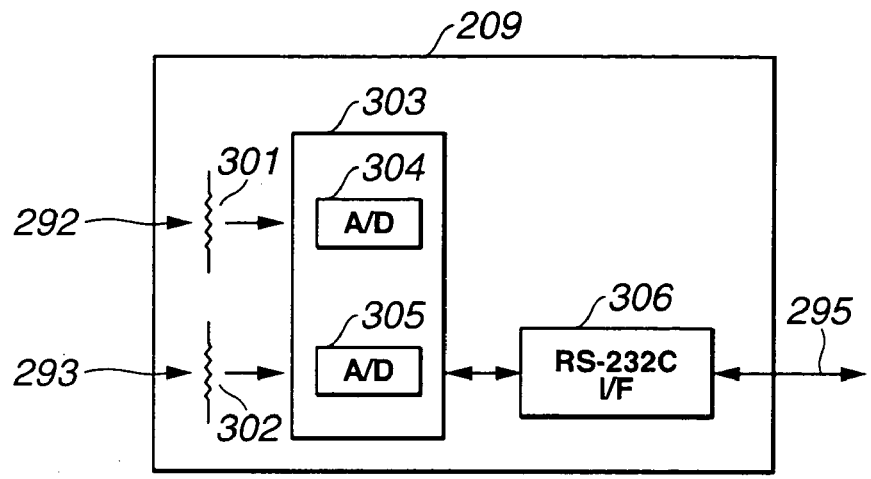
FIG. 18 is a block diagram showing the circuitry of the remote controller employed in the endoscope system including the third embodiment of the present invention.
Figure 19:
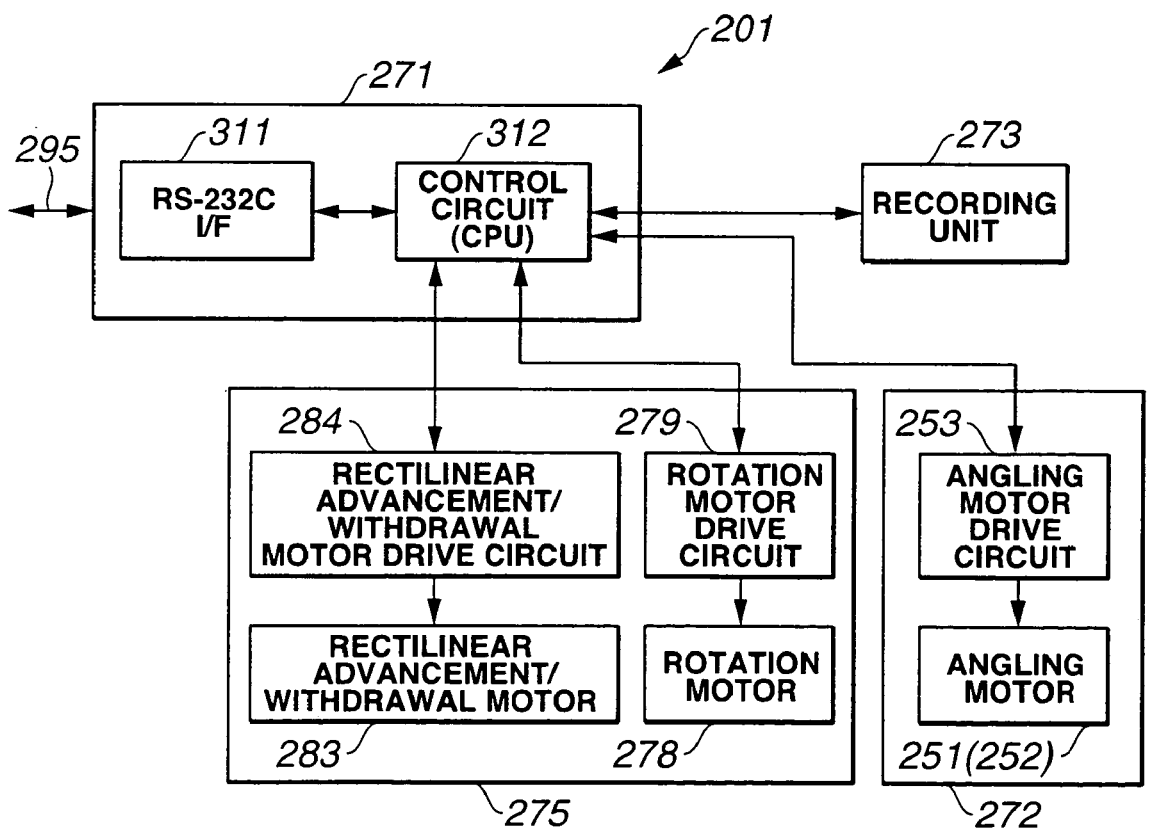
FIG. 19 is a block diagram showing the circuitry of the electrically angled endoscope system including the third embodiment of the present invention.

FIG. 15 to FIG. 19 are concerned with a third embodiment of the present invention. FIG. 15 is a perspective view of an electrically angled endoscope system. FIG. 16 is a perspective view of a remote controller. FIG. 17 is a sectional view of a driving motor unit. FIG. 18 is a block diagram showing the circuitry of the remote controller. FIG. 19 is a block diagram showing the circuitry of the electrically angled endoscope system.

In the description of the third embodiment to be made in conjunction with FIG. 15 to FIG. 19, the same reference numerals will be assigned to components identical to those of the first and second embodiments shown in FIG. 1 to FIG. 13. The description of the components will be omitted.

(Structure)

According to the first and second embodiments shown in FIG. 1 to FIG. 13, the bending section is manually bent using the angling knobs 51 and 52. According to the third embodiment, the bending section is electrically bent.

As shown in FIG. 15, an electrically angled endoscope system 201 has angling wires 31, 32, 33, and 34 (see FIG. 3), which lie through an endoscope 202, pulled by angling motors 251 and 252.

The electrically angled endoscope system 201 has a receiving unit 3 and a monitor 4 incorporated thereinto.

Moreover, the electrically angled endoscope system 201 comprises a control unit 271 that controls the entire system and an angling motor unit 272 that drives the angling motors 251 and 252.

Furthermore, the electrically angled endoscope system 201 includes a recording unit 273 that records received images.

The electrically angled endoscope system 201 has a remote controller 209 extended from a housing 207 thereof.

The angling motors 251 and 252 are actuated using a joystick 291 included in the remote controller 209.

Furthermore, a drum 274 about which an inserting unit 110 is wound is incorporated in the housing 207.

Moreover, as shown in FIG. 15 and FIG. 17, a protective tube 39 lies, similarly to that included in the second embodiment, through the inserting unit main body 111 of the inserting unit 110. A driving motor unit 275 for driving a guide member 106 sheathed in the protective tube 39 is disposed near the proximal end of the inserting unit main body 111.

The driving motor unit 275 rotates or rectilinearly advances or withdraws the guide member 106 (see FIG. 10) on behalf of the holding member manipulation lever 61 included in the first embodiment or the guide member manipulation handle 162 included in the second embodiment. The remote controller 209 and driving motor unit 275 constitute a moving means.

Next, the remote controller 209 will be described in conjunction with FIG. 16.

As shown in FIG. 16, in addition to the joystick 291, a freeze switch that is used to instruct or cancel freezing of an image, and a menu switch that is used to display a menu, a rectilinear advancement/withdrawal lever 292 and a rotating handle 293 are disposed on the operating surface of the remote controller 209.

The rectilinear advancement/withdrawal lever 292 and rotating handle 293 are associated with the movements enabled by the driving motor unit 275.

A remote controller cable 295 is coupled to the remote controller 209.

Next, the driving motor unit 275 will be described below.

As shown in FIG. 17, the driving motor unit 275 has a linkage shaft 163, a linkage shaft holding unit 254, and a rotary motor holding chamber 277 incorporated in a connector case 276.

The rotary motor holing chamber 277 does not rotate by itself but accommodates a rotary motor 278.

The rotation shaft of the rotary motor 278 is coupled to the linkage shaft 163. The rotary motor 278 rotates the linkage shaft 163 in response to a directive given from a rotary motor drive circuit 279.

A lever 280 is extended from the rotary motor holding chamber 277. The tip of the lever 280 is terminated at a rack 281.

Moreover, the connector case 276 accommodates a pinion 282, a rectilinear advancement/withdrawal motor 283, and a rectilinear advancement/withdrawal motor drive circuit 284.

The pinion 282 is meshed with the rack 281. The rectilinear advancement/withdrawal motor 283 rotates the pinion 282 in response to a directive issued from the internal rectilinear advancement/withdrawal motor drive circuit 284.

The movements of the rack 281 and pinion 282 respectively are limited to a range defined by a groove 285 formed in the internal wall of the driving motor unit 275.

Next, referring to FIG. 18, the circuitry of the remote controller 209 will be described below.

As shown in FIG. 18, the rectilinear advancement/withdrawal lever 292 of the remote controller 209 includes a variable resistor 301 whose resistance varies depending on the position of the rectilinear advancement/withdrawal lever 292.

Moreover, the rotating handle 293 of the remote controller 209 includes a variable resistor 302 whose resistance varies depending on an angle of rotation by which the rotating handle 293 is rotated.

Furthermore, the remote controller 209 includes a remote controller control circuit (hereinafter, a remote controller CPU) 303 and an RS-232C interface 306.

In the remote controller CPU 303, A/D converters 304 and 305 analog-to-digital convert and output signals sent from the variable resistors 301 and 302 respectively.

The RS-232C interface 306 converts the signals sent from the remote controller CPU 303 into signals conformable to the RS-232C standard, and places the resultant signals on the remote controller cable 295.

A signal produced responsively to the manipulation of any switch other than the freeze switch included in the remote controller 209 is fetched into an input/output port of the remote controller CPU 303, and transferred to the RS-232C interface 306.

Next, referring to FIG. 19, the circuitry of the electrically angled endoscope system 201 will be described below.

The control unit 271 is responsible for control of the entire electrically angled endoscope system 201. The control unit 271 includes an RS-232C interface 311 and a control circuit (CPU) 312.

The recording unit 273 is connected to the control circuit 312 and records an endoscope image acquired by the capsular head unit 41 shown in FIG. 15.

As shown in FIG. 19, the angling motor unit 272 includes the angling motors 251 and 252 and the angling motor drive circuit 253, and controls the bending section 13 of the endoscope 202 shown in FIG. 15.

As shown in FIG. 19, the driving motor unit 275 serving as a driving means drives the rectilinear advancement/withdrawal motor 283 and rotary motor 278.

(Operation)

In the third embodiment, when the rectilinear advancement/withdrawal lever 292 of the remote controller 209 is manipulated, a signal the variable resistor 301 produces responsively to the manipulation is transferred to the remote controller CPU 303 incorporated in the remote controller.

The signal produced responsively to the manipulation of the rectilinear advancement/withdrawal lever 292 is converted into a digital form by the A/D converter 304, and fetched into the remote controller CPU 303.

The remote controller CPU 303 places the fetched signal on the remote controller cable 295 via the RS-232C interface 306 as position information on the position of the rectilinear advancement/withdrawal lever 292.

The digital signal representing the position information on the position of the rectilinear advancement/withdrawal lever 292 is transferred to the RS-232C interface 311 included in the control unit 271 over the remote controller cable 295, and fetched into the control circuit 312.

The control circuit 312 performs predetermined processing to verify that the signal is addressed to the driving motor unit 275, and transmits the signal to the rectilinear advancement/withdrawal motor drive circuit 284 included in the driving motor unit 275. The rectilinear advancement/withdrawal motor drive circuit 284 actuates the rectilinear advancement/withdrawal motor 283 according to the received position information.

When the rotating handle 293 of the remote controller 209 is manipulated, a signal the variable register 302 produces responsively to the manipulation is transferred to the remote controller CPU 303 incorporated in the remote controller.

The signal produced responsively to the manipulation of the rotating handle 293 is converted into a digital form by the A/D converter 305, and fetched into the remote controller CPU 303.

The remote controller CPU 303 places the received signal on the remote controller cable 295 via the RS-232C interface 306 as position information on the position of the rotating handle 293.

The digital signal representing the position information on the position of the rotating handle 293 is transferred to the RS-232C interface 311 included in the control unit 271 over the remote controller cable 295, and fetched into the control circuit 312.

The control circuit 312 performs predetermined processing to verify that the signal is addressed to the driving motor unit 275, and transmits the signal to the rotary motor drive circuit 279 included in the driving motor unit 275. Furthermore, the rotary motor drive circuit 279 actuates the rotary motor 278 according to the received position information.

Likewise, when angling is directed by manipulating the joystick 291 of the remote controller 209, an operational signal (position information) produced responsively to the manipulation of the joystick 291 is digitized, and transferred to the control unit 271 via the RS-232C interface 306. Furthermore, the angling motor drive circuit 253 included in the angling motor unit 272 drives the angling motors 251 and 252 according to the position information given using the joystick 291. consequently, the linkage shaft 163 rotates or moves back and forth. This causes the guide member 106 to rotate or move back and forth. Furthermore, the bending section 13 is bent in any direction. Eventually, the capsular head unit 41 is angled in any direction.

(Advantages)

According to the third embodiment, the endoscope is angled electrically, though the endoscopes of the first and second embodiments are angled manually. This results in little fatigue and improved examination efficiency.

Fourth Embodiment

Figure 20:
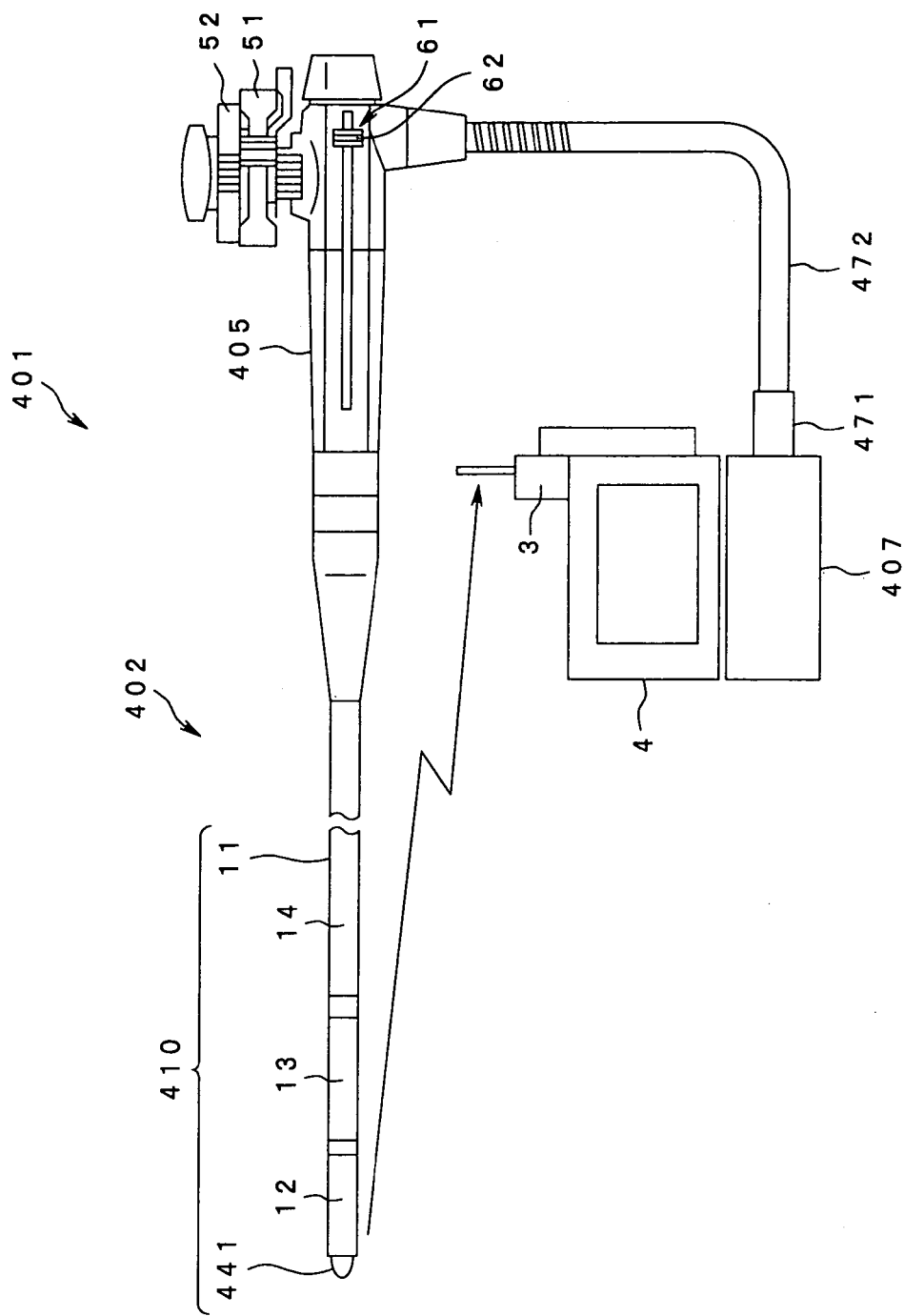
FIG. 20 is a side view of an electronic endoscope system including a fourth embodiment of the present invention.
Figure 21:
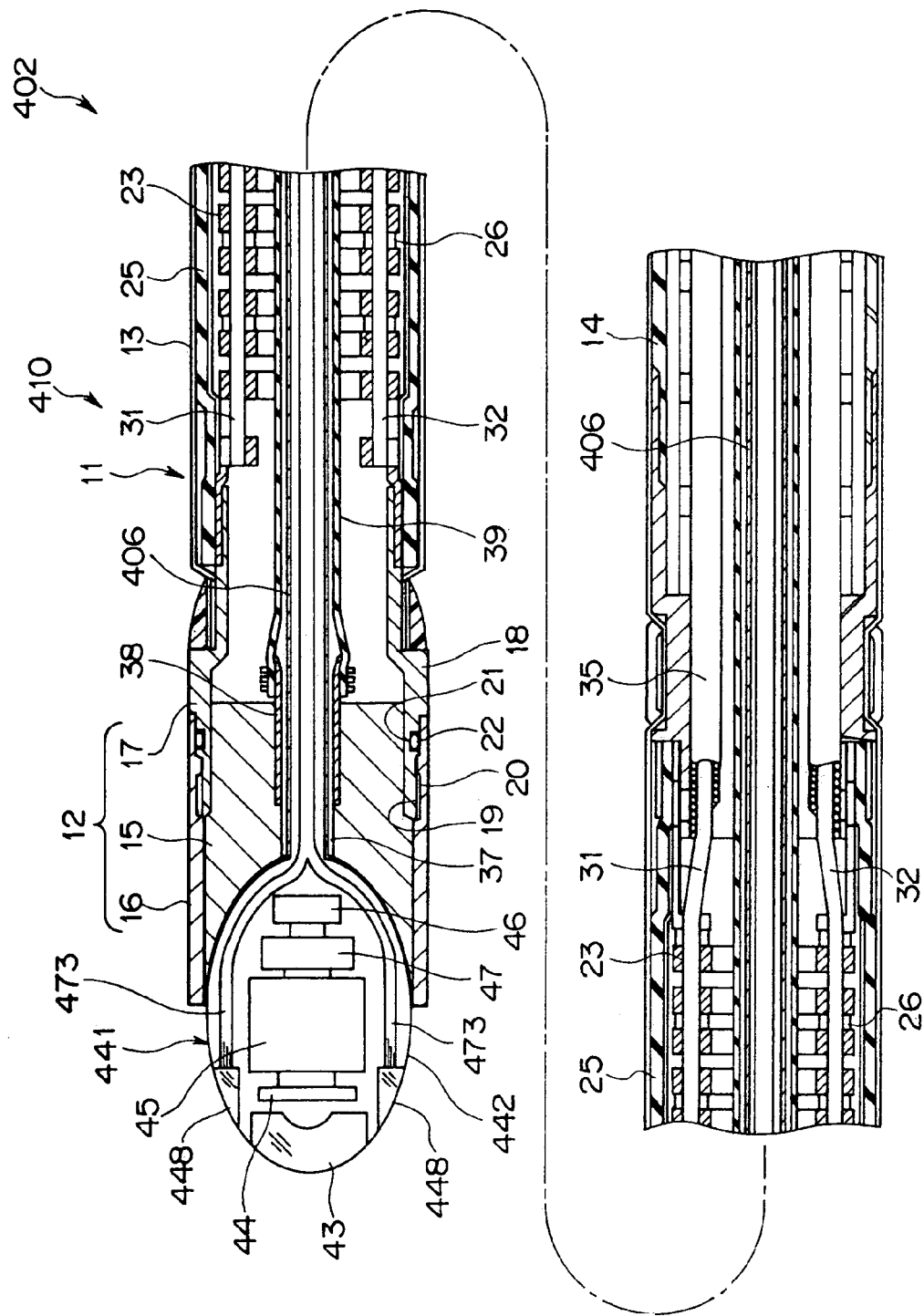
FIG. 21 is a sectional view of an inserting unit of an endoscope in accordance with the fourth embodiment of the present invention.
Figure 22:
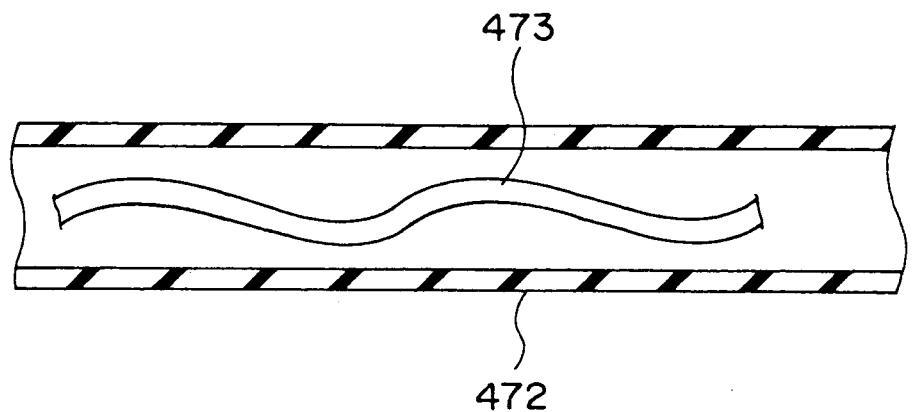
FIG. 22 is a sectional view of a universal cord included in the fourth embodiment of the present invention.

FIG. 20 to FIG. 22 are concerned with a fourth embodiment of the present invention. FIG. 20 is a side view of an electronic endoscope system. FIG. 21 is a side view of an inserting unit of an endoscope. FIG. 22 is a sectional view of a universal cord.

In the description of the fourth embodiment to be made in conjunction with FIG. 20 to FIG. 22, the same reference numerals will be assigned to components identical to those of the first and second embodiments shown in FIG. 1 to FIG. 13. The description of the components will be omitted.

(Structure)

As shown in FIG. 20, an electronic endoscope system 401 comprises an endoscope 402, a receiving unit 3, a monitor 4, and a light source unit 407.

The endoscope 402 includes a connector 471 that is coupled to the light source unit 407 and a universal cord 472 that links the connector 471 and an operating unit 405.

As shown in FIG. 22, a light guide 473 is contained in the universal cord 472. The light guide 473 is coupled to a lamp, which is not shown, included in the light source unit 407 shown in FIG. 20, whereby illumination light is propagated over the light guide 473.

As shown in FIG. 21, the distal parts of the light guide 473 are locked in a capsular case 442 of a capsular head unit 441 attached to the distal end of an inserting unit 410.

Illumination windows 448 through which illumination light propagated over the light guide 473 is spread and irradiated are located in front of the distal parts of the light guide 473.

A holding member 406 is, instead of the holding member 6 (see FIG. 2) included in the first embodiment, coupled as a holding means, which holds the capsular head unit so that the capsular head unit can be freely separated from or restored to the inserting unit, to the proximal end of the capsular head unit 41. The holding member 406 is a tubular member made of a super-elastic alloy.

The light guide 473 lies through the holding member 406 that is a tubular member, and passes through the universal cord 472 shown in FIG. 22.

The capsular head unit 441 shown in FIG. 21 can be freely advanced or withdrawn by means of the holding member 406. The light guide 473 has an extra length equivalent to a degree to which the holding member 406 is advanced or withdrawn, and is therefore, as shown in FIG. 22, tortuously contained in the universal cord 472.

(Operation)

According to the fourth embodiment, the capsular head unit 441 can freely be jutted out of the inserting unit main body 11 by moving the holding member 406. At this time, the light guide 473 repeatedly becomes tortuous or straight along with the advancement or withdrawal the light guide 473 makes after being jutted out.

Incidentally, illumination light is supplied from the light source unit 407, propagated over the light guide 473 that lies through the connector 471, universal cord 472, and inserting unit main body 11, and irradiated to an object through the illumination windows 448 formed in the capsular head unit 441. The transmitting unit 46 transmits an image signal that represents an object image picked up by the CCD type solid-state image pickup device 44. Consequently, the object can be visualized.

(Advantages)

According to the fourth embodiment, since illumination light supplied from outside is adopted, power developed by the power supply unit 47 incorporated in the capsular head unit 441 can be fed exclusively to the CCD type solid-state image pickup device 44. Exhaustion of the power supply unit 47 can be minimized.

According to the fourth embodiment, the means for jutting the capsular head unit 441 is not limited to the structure employed in the first embodiment. Alternatively, the structure employed in the second or third embodiment will do.

Fifth Embodiment

Figure 23:
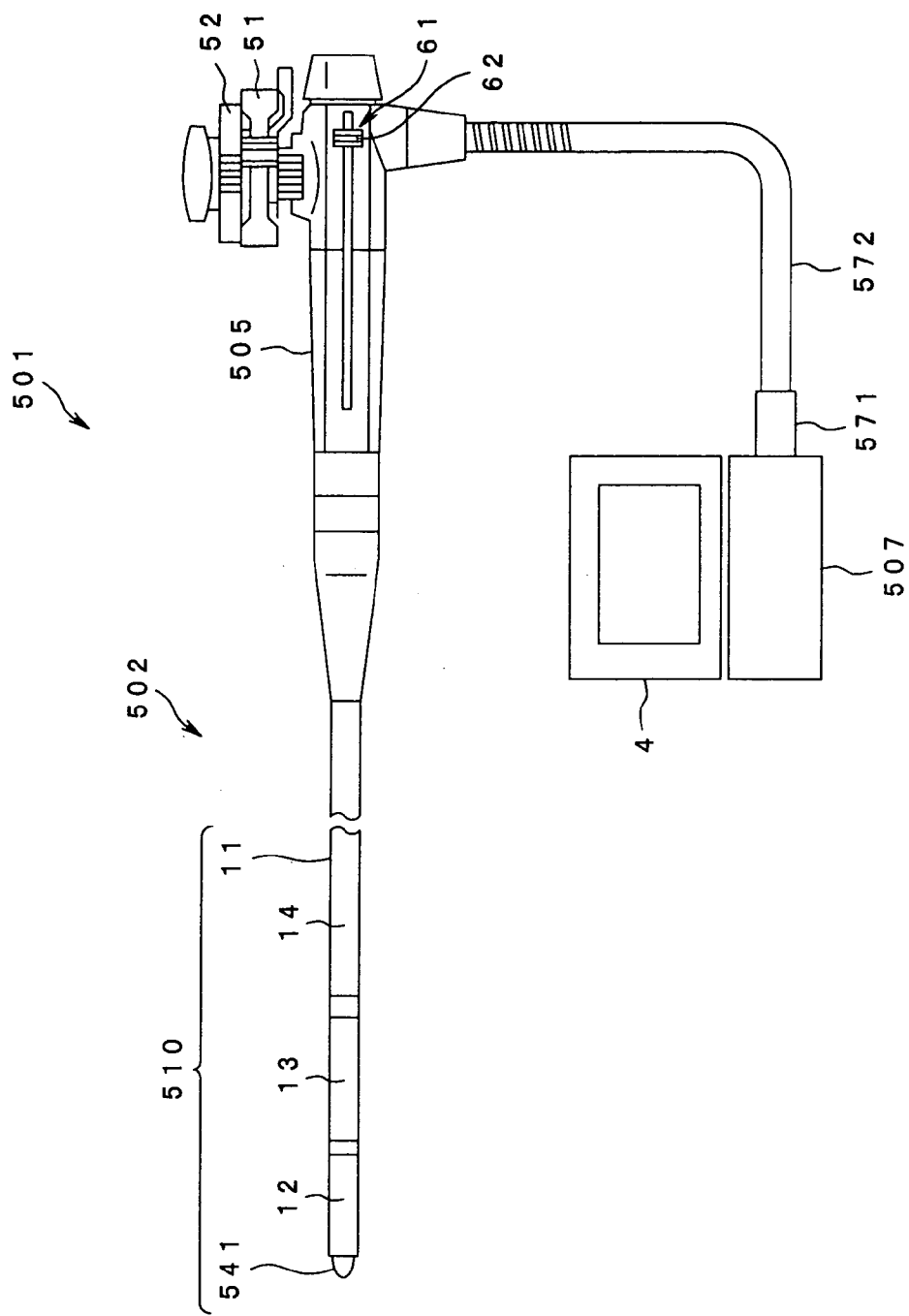
FIG. 23 is a side view of an electronic endoscope system including a fifth embodiment of the present invention.

FIG. 23 and FIG. 24 are concerned with a fifth embodiment of the present invention. FIG. 23 is a side view of an electronic endoscope system, and FIG. 24 is a sectional view of an inserting unit of an endoscope.

In the description of the fifth embodiment to be made in conjunction with FIG. 23 and FIG. 24, the same reference numerals will be assigned to components identical to those of the first to fourth embodiments shown in FIG. 1 to FIG. 22. The description of the components will be omitted.

(Structure)

As shown in FIG. 23, an electronic endoscope system 501 comprises an endoscope 502, a monitor 4, and a camera control unit 507.

The endoscope 502 includes a connector 571 that is coupled to the camera control unit 507 and a universal cord 572 that links the connector 571 and an operating unit 505.

A signal line 573 shown in FIG. 24 and coupled to the camera control unit 507 is contained in the universal cord 572.

As shown in FIG. 24, one end of the signal line 573 is locked in a capsular case 542 of a capsular head unit 541 attached to the distal end of an inserting unit 510.

Moreover, a CCD type solid-state image pickup device 44 is located beyond the distal end of the signal line 573 with a connection substrate 545 between them.

Furthermore, the signal line 573 lies through a holding member 406 that is a tubular body and passes through the universal cord 572 shown in FIG. 23. The signal line 573 is coupled to the CCD type solid state image pickup device 44.

As shown in FIG. 24, the capsular head unit 541 can be freely advanced or withdrawn by means of the holding member 406. The signal line 573 has an extra length equivalent to the degree to which the capsular head unit is advanced or withdrawn, and is, similarly to the light guide 473 shown in FIG. 19, tortuously contained in the universal cord 572 shown in FIG. 23.

(Operation)

According to the fifth embodiment, the capsular head unit 541 can be freely jutted out. At this time, the signal line 573 repeatedly becomes tortuous or straight along with the advancement or withdrawal the capsular head unit makes after being jutted out.

(Advantages)

According to the foregoing structure, the CCD type solid-state image pickup device 44 is driven by the camera control unit 507 located outside. Consequently, power developed by the power supply unit 47 incorporated in the capsular head unit 541 can be fed exclusively to the LEDs 48. Eventually, exhaustion of the power supply unit 47 can be minimized.

According to the fifth embodiment, the means for jutting out the capsular head unit 541 is not limited to the structure employed in the first embodiment. Alternatively the structure employed in the second or third embodiment will do.

Incidentally, a visualizing means for visualizing an object may not be realized with the CCD type solid-state image pickup device 44, but may be realized with an image guide fiber (not shown) coupled to an eyepiece unit (not shown) included in an operating unit.

Figure 25:
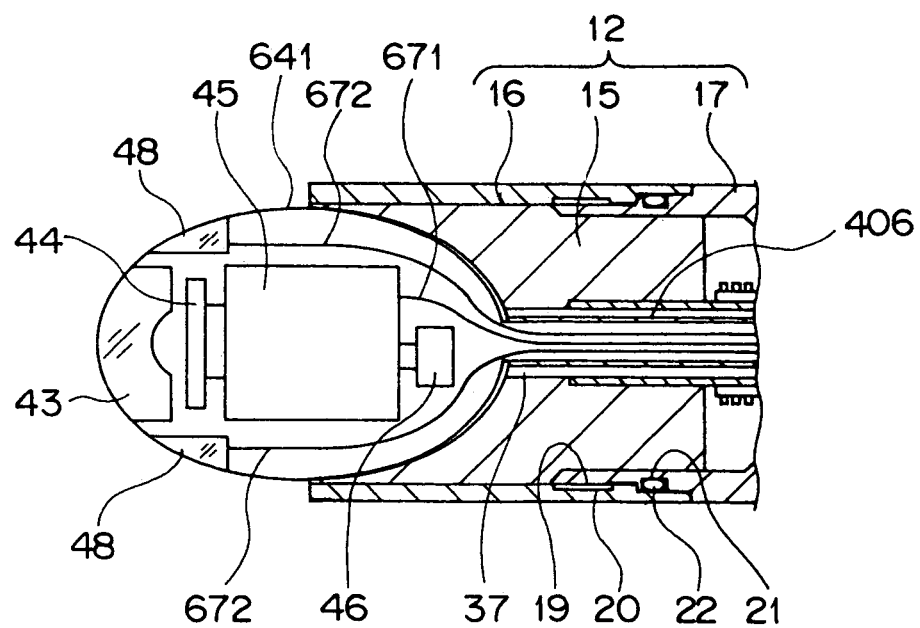
FIG. 25 is a sectional view of the distal portion of an inserting unit included in a variant of the fifth embodiment of the present invention.

FIG. 25 is a sectional view of a distal portion of an inserting unit included in a variant of the fifth embodiment.

As shown in FIG. 25, according to the present variant, a capsular head unit 641 includes a CCD type solid-state image pickup device 44 as an image pickup sensor and LEDs 48 as an illuminating means. An image pickup sensor power supply line 671 and an illumination power supply line 672 over which power is supplied to the CCD solid-state image pickup device 44 and LEDs 48 respectively are contained in the capsular head unit 641 and a holding member 406 alike. In this case, image information sent from the CCD solid-state image pickup device 44 is transmitted by radio to the receiving unit 3 via the camera control unit 45 and transmitting unit 46.

According to the variant, similarly to the fifth embodiment shown in FIG. 23 and FIG. 24, exhaustion of the power supply unit incorporated in the capsular head unit 641 can be minimized. Otherwise, the capsular head unit 641 may be devoid of the power supply unit.

Apparently, it is preferred that the objective optical systems incorporated in the respective capsular head units shown in FIG. 1 to FIG. 25 support a variety of viewing angles or focal lengths irrespective of whether the objective optical systems are of a monocular or binocular type or of a side-vision or oblique-vision type.

The aforesaid embodiments may be used in combination within the scope of the present invention defined in the appended claims.

As described so far, according to the present invention, a head unit including a visualizing means is freely detachably attached to the distal end of an inserting unit main body. Illumination light can be irradiated so that an optimal view image can be produced. A stable visualization capability can be maintained.

Moreover, according to the present invention, a head unit including a visualizing means is freely detachably attached to the distal end of an inserting unit main body. Moreover, the head unit can be accurately and readily moved from the distal end of the inserting unit main body to a desired position. Consequently, a range that can be examined will expand and the desired position can be readily accessed.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

The invention claimed is:

1. An endoscope, comprising:
    an inserting unit main body;
    and a head unit that is freely detachably attached to the distal end of the inserting unit main body and that includes a visualizing means for visualizing an object and an illuminating means for irradiating illumination light to the object, wherein:
    the head unit is held by the holding member extending in the inserting unit main body;
    the holding member is realized with an elastic member; and
    the holding member has a predetermined bent shape, wherein distal extension of the holding member angles the head unit in a radial direction orthogonal to a longitudinal axis of the distal end of the inserting unit main body.

2. The endoscope according to claim 1, further comprising a transmitting means that is included in the head unit and that transmits an image signal which represents an image of the object visualized by the visualizing means.

3. The endoscope according to claim 2, further comprising a holding member that has a predetermined length, wherein:
    the head unit is held by the holding member lying through the inserting unit main body.

4. The endoscope according to claim 1, wherein the illuminating means irradiates light, which is emitted from a light source unit and supplied to the head unit through the distal end of the inserting unit main body over a light guide fiber contained in the holding member, as illumination light from the head unit.

5. endoscope according to claim 1, wherein the illuminating means is realized with a light emitting element incorporated in the head unit.

6. The endoscope according to claim 1, further comprising a manipulating means for causing the head unit to move while being held so that the head unit will be attached or detached to or from the distal end of the inserting unit main body.

7. The endoscope according to claim 6, wherein the manipulating means is used to freely separate or restore the head unit from or to the inserting unit main body in an axial direction of the inserting unit main body.

8. The endoscope according to claim 6, wherein the manipulating means is used to freely separate or restore the head unit from or to the inserting unit main body in a radial direction of the inserting unit main body.

9. An endoscope, comprising:
    an inserting unit main body;
    a head unit that is freely detachably attached to the distal end of the inserting unit main body and that includes a visualizing means for visualizing an object and an illuminating means for irradiating illumination light to the object;
    a holding member that lies through the inserting unit main body, the holding unit is realized with an elastic member, the holding member having a predetermined bent shape, and having a predetermined length required to hold the head unit; and
    a moving means for moving the head unit back and forth with the head unit held so that the head unit will be attached or detached to or from the distal end of the inserting unit main body,
    wherein distal extension of the holding member angles the head unit in a radial direction orthogonal to a longitudinal axis of the distal end of the inserting unit main body.

10. The endoscope according to claim 9, wherein the moving means includes a motor driving means, and the motor driving means enables the back and forth movements.

11. The endoscope according to claim 10, wherein the motor driving means rotates the head unit about the inserting axis of the inserting unit main body.

12. The endoscope according to claim 9, further comprising a transmitting means that is incorporated in the head unit and that transmits an image signal which represents an image of the object visualized by the visualizing means.

13. An endoscope, comprising:
- an inserting unit main body that receives illumination light supplied from a light source over a light guide fiber and that propagates the illumination light to the distal end thereof;
- a head unit that is freely detachably attached to the distal end of the inserting unit main body, and that includes an illumination window through which illumination light supplied over the light guide fiber is irradiated to an object, an image pickup sensor which picks up an image of the object, and a transmitting unit which transmits a signal representing an image of the object acquired by the image pickup sensor;
- an operating unit for causing the head unit to move back and forth while being held so that the head unit will be attached or detached to or from the distal end of the inserting unit main body; and
- a tubular holding member that has a predetermined length, wherein:
- the head unit is held by the holding member lying through the inserting unit main body;
- the holding member is realized with an elastic member; and
- the holding member has a predetermined bent shape, wherein distal extension of the holding member angles the head unit in a radial direction orthogonal to a longitudinal axis of the distal end of the inserting unit main body.

14. The endoscope according to claim 13, wherein: the light guide fiber is contained in the tubular holding member.

15. An endoscope, comprising:
- an inserting unit main body;
- a head unit that is freely detachably attached to the distal end of the inserting unit main body and that includes an image pickup sensor which picks up an image of an object and a light emitting element which irradiates illumination light to the object; and
- a tubular holding member that lies through the inserting unit main body, the tubular holding member is realized with an elastic member, the tubular holding member has a predetermined bent shape, a predetermined length, and holds the head unit, wherein:
- a signal line extending from the image pickup sensor lies through the tubular holding member, and distal extension of the holding member angles the head unit in a radial direction orthogonal to a longitudinal axis of the distal end of the inserting unit main body.

16. The endoscope according to claim 15, further comprising a power supply unit that is incorporated in the head unit and that supplies power to the light emitting element.

17. The endoscope according to claim 15, further comprising a power line over which power is supplied to the light emitting element and which lies through the tubular holding member.

* * * * *